US012685476B2

(12) United States Patent
Krishnan et al.

(10) Patent No.: US 12,685,476 B2
(45) Date of Patent: Jul. 21, 2026

(54) SYSTEM AND METHOD FOR SALIENCY DETECTION IN LONG-TERM ECG MONITORING

(71) Applicants: Sridhar Krishnan, Richmond Hill (CA); Sourav Kumar Mukhopadhyay, Scarborough (CA)

(72) Inventors: Sridhar Krishnan, Richmond Hill (CA); Sourav Kumar Mukhopadhyay, Scarborough (CA)

( * ) Notice: Subject to any disclaimer, the term of this patent is extended or adjusted under 35 U.S.C. 154(b) by 497 days.

(21) Appl. No.: 18/016,391

(22) PCT Filed: Jul. 16, 2021

(86) PCT No.: PCT/CA2021/050988

§ 371 (c)(1),
(2) Date: Jan. 16, 2023

(87) PCT Pub. No.: WO2022/011480

PCT Pub. Date: Jan. 20, 2022

(65) Prior Publication Data

US 2023/0277111 A1     Sep. 7, 2023

Related U.S. Application Data

(60) Provisional application No. 63/052,826, filed on Jul. 16, 2020.

(51) Int. Cl.
*A61B 5/366*          (2021.01)
*A61B 5/00*           (2006.01)
(Continued)

(52) U.S. Cl.
CPC .............. *A61B 5/366* (2021.01); *A61B 5/352* (2021.01); *A61B 5/364* (2021.01); *A61B 5/7203* (2013.01); *A61B 5/7257* (2013.01); *A61B 5/7264* (2013.01)

(58) Field of Classification Search
None
See application file for complete search history.

(56) References Cited

U.S. PATENT DOCUMENTS

2017/0238909 A1 * 8/2017 Shin ..................... A61B 5/7267
2019/0384757 A1 * 12/2019 Garrett ................. A61B 5/7203
(Continued)

FOREIGN PATENT DOCUMENTS

WO      WO-2021037101 A1 * 3/2021    ............. A61B 5/318

*Primary Examiner* — Kennedy Schaetzle
(74) *Attorney, Agent, or Firm* — Gowling WLG (Canada) LLP

(57)          ABSTRACT

There is provided a computer-implemented method for identifying abnormal QRS-complexes in an ECG signal comprising: receiving an ECG signal with detected QRS-complexes; calculating and normalizing a plurality of geometric measures of the QRS-complexes; constructing an RGB image with three two-dimensional matrices, each matrix corresponding to one of the calculated plurality of geometric measures, the geometric measures belonging to one QRS-complex have the same matrix index across the three two-dimensional matrices; transforming the RGB image to a plurality of gray-scale images; computing histograms of each of the plurality of gray-scale image; iteratively comparing every histogram peak to its previous one; and marking pixel intensities corresponding to histogram peaks with a difference value of equal or greater than a predefined threshold referred to as a saliency threshold, as salient pixels; using saliency detection for mapping salient pixels indices onto the ECG signal and classifying the salient pixel indices as abnormal QRS complexes.

18 Claims, 36 Drawing Sheets

(51) Int. Cl.
*A61B 5/352* (2021.01)
*A61B 5/364* (2021.01)

(56) References Cited

U.S. PATENT DOCUMENTS

2020/0178825 A1* 6/2020 Lu ......................... G06N 3/045
2021/0106248 A1* 4/2021 Du ......................... G06T 11/60

* cited by examiner

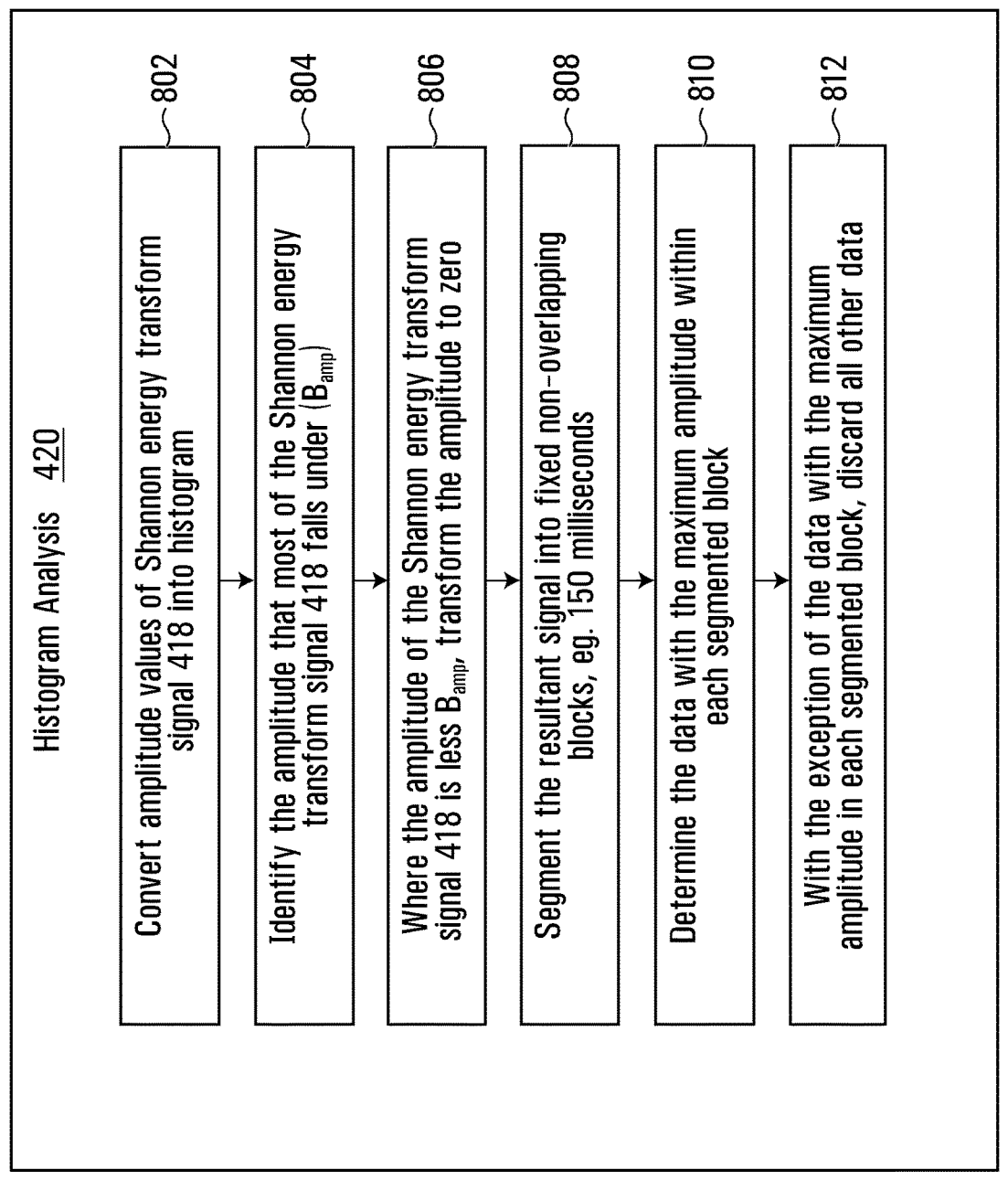

Histogram Analysis  420

802 — Convert amplitude values of Shannon energy transform signal 418 into histogram 804 — Identify the amplitude that most of the Shannon energy transform signal 418 falls under ($B_{amp}$)

806 — Where the amplitude of the Shannon energy transform signal 418 is less $B_{amp}$, transform the amplitude to zero 808 — Segment the resultant signal into fixed non-overlapping blocks, eg. 150 milliseconds 810 — Determine the data with the maximum amplitude within each segmented block 812 — With the exception of the data with the maximum amplitude in each segmented block, discard all other data

FIG. 8

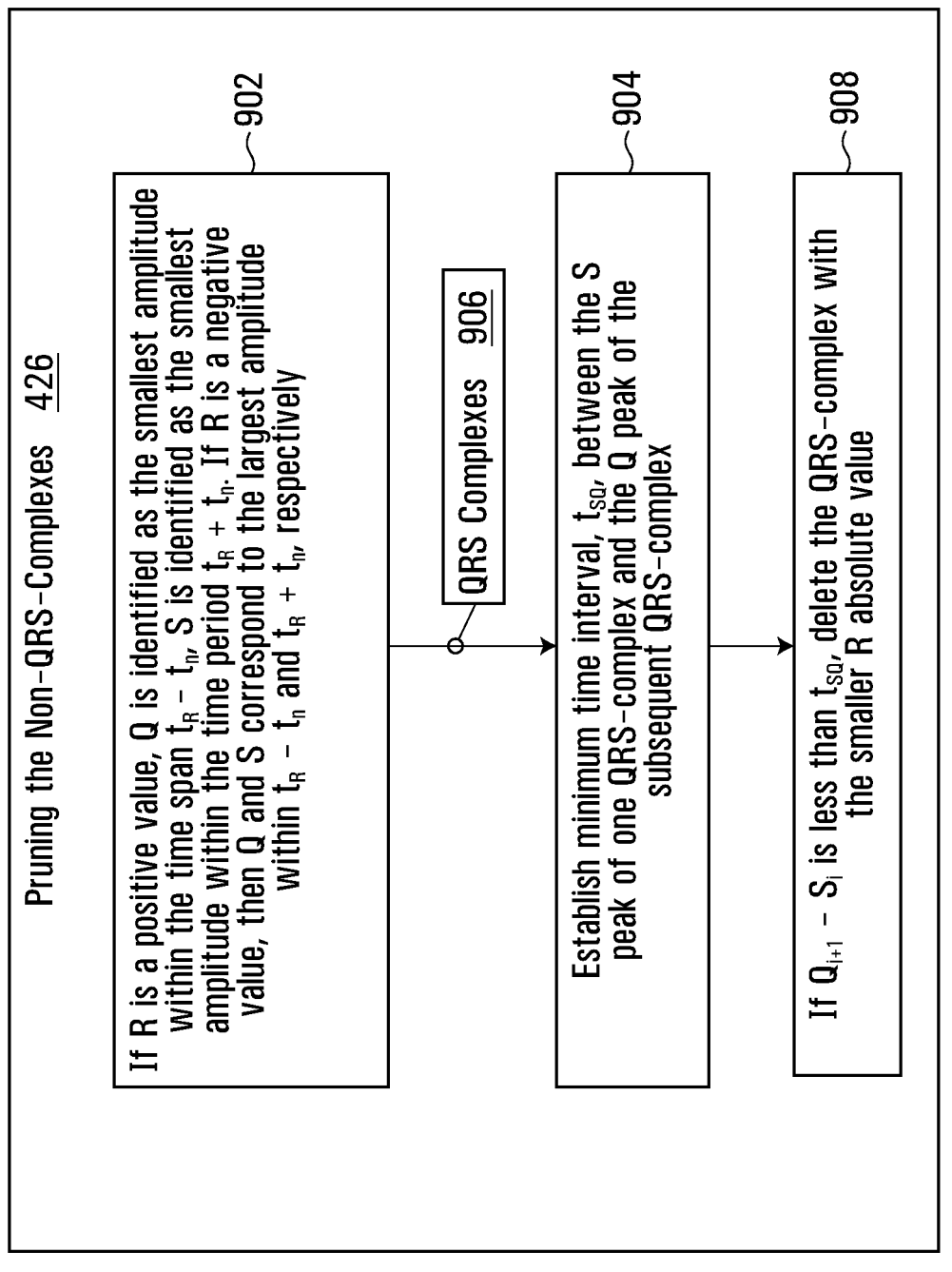

Pruning the Non-QRS-Complexes  426

If R is a positive value, Q is identified as the smallest amplitude within the time span $t_R - t_n$, S is identified as the smallest amplitude within the time period $t_R + t_n$. If R is a negative value, then Q and S correspond to the largest amplitude within $t_R - t_n$ and $t_R + t_n$, respectively

902

QRS Complexes  906

Establish minimum time interval, $t_{SQ}$, between the S peak of one QRS-complex and the Q peak of the subsequent QRS-complex

904

If $Q_{i+1} - S_i$ is less than $t_{SQ}$, delete the QRS-complex with the smaller R absolute value

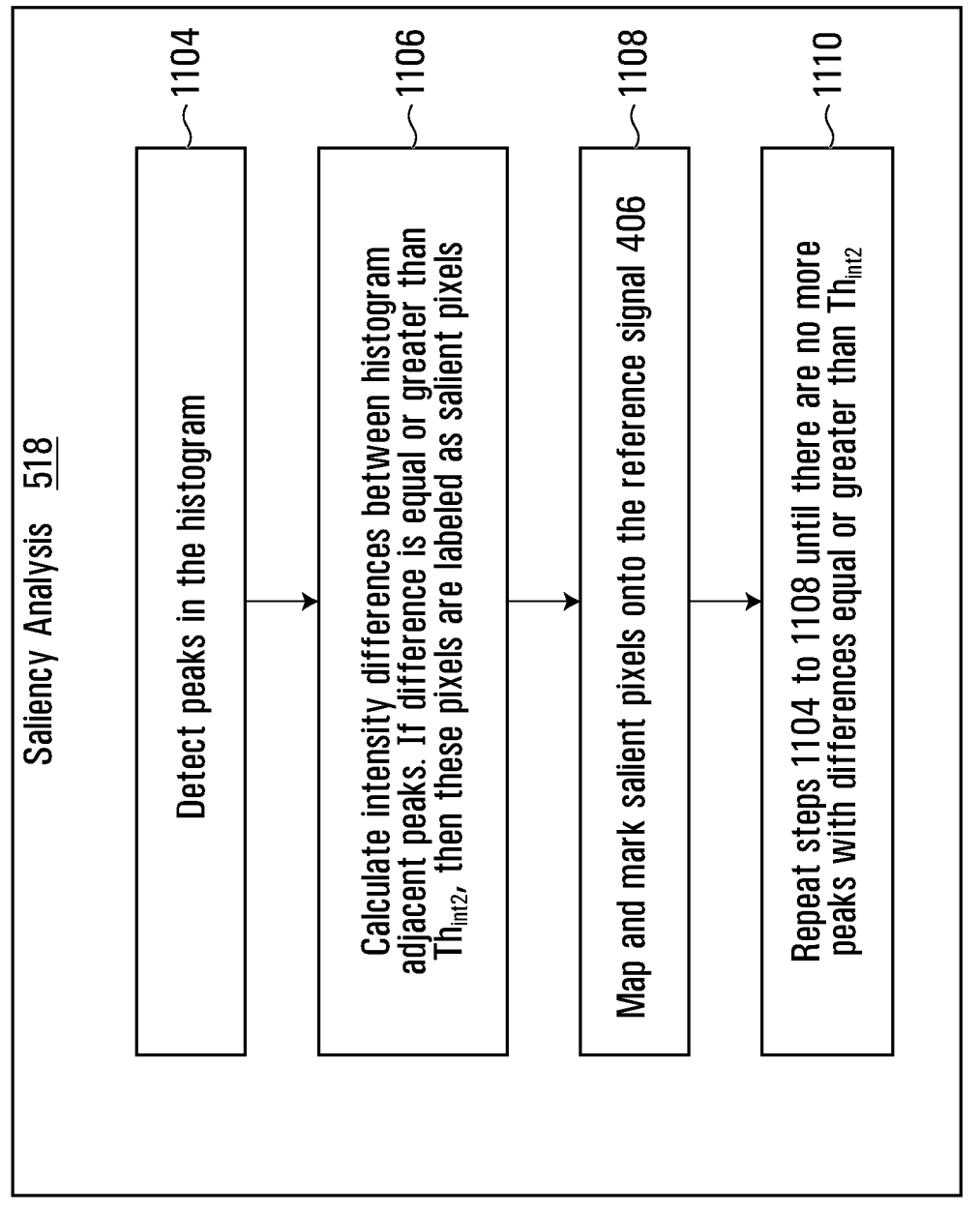

Saliency Analysis  518

Detect peaks in the histogram — 1104

Calculate intensity differences between histogram adjacent peaks. If difference is equal or greater than $Th_{int2r}$ then these pixels are labeled as salient pixels — 1106

Map and mark salient pixels onto the reference signal 406 — 1108

Repeat steps 1104 to 1108 until there are no more peaks with differences equal or greater than $Th_{int2}$ — 1110

FIG. 11

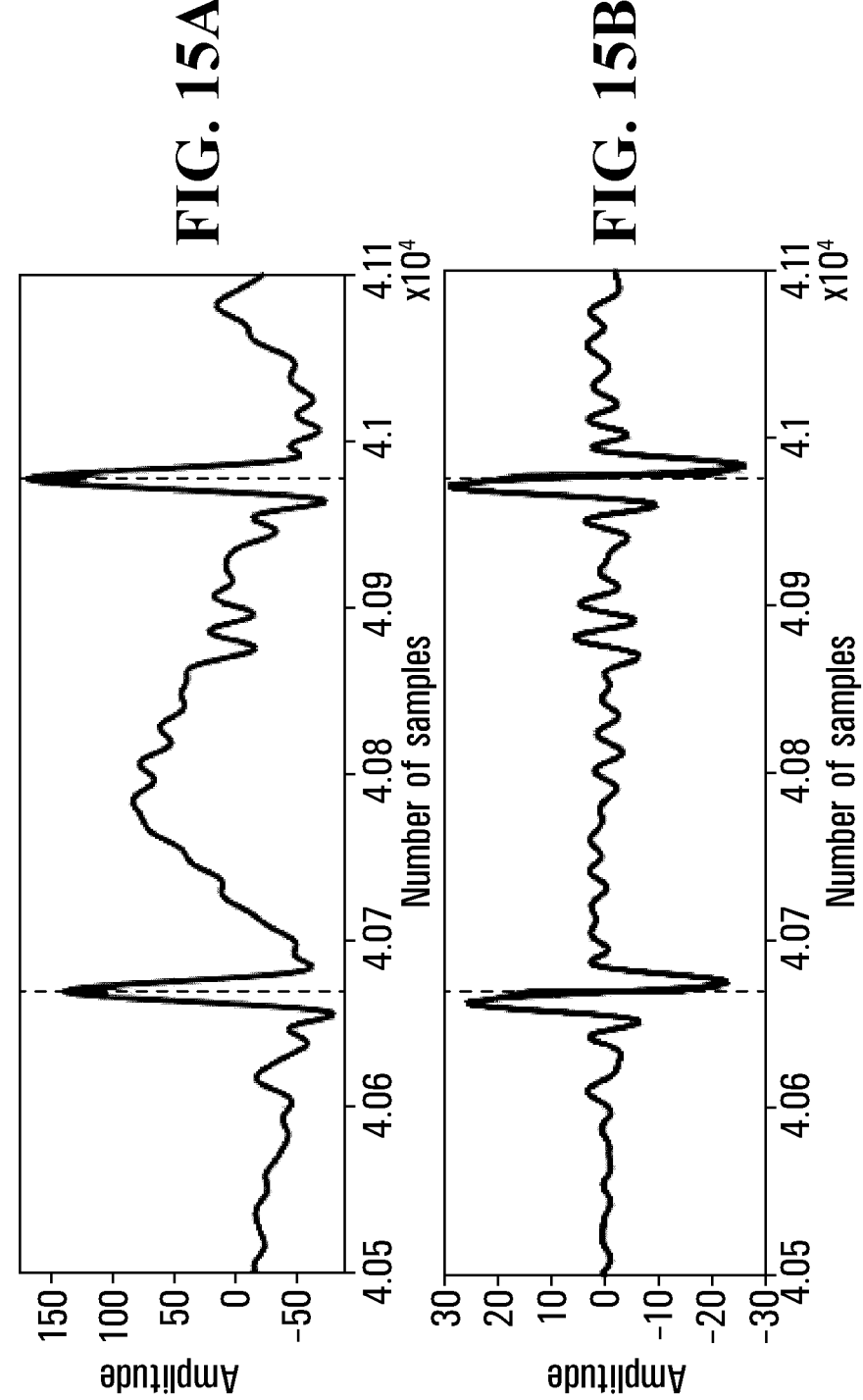

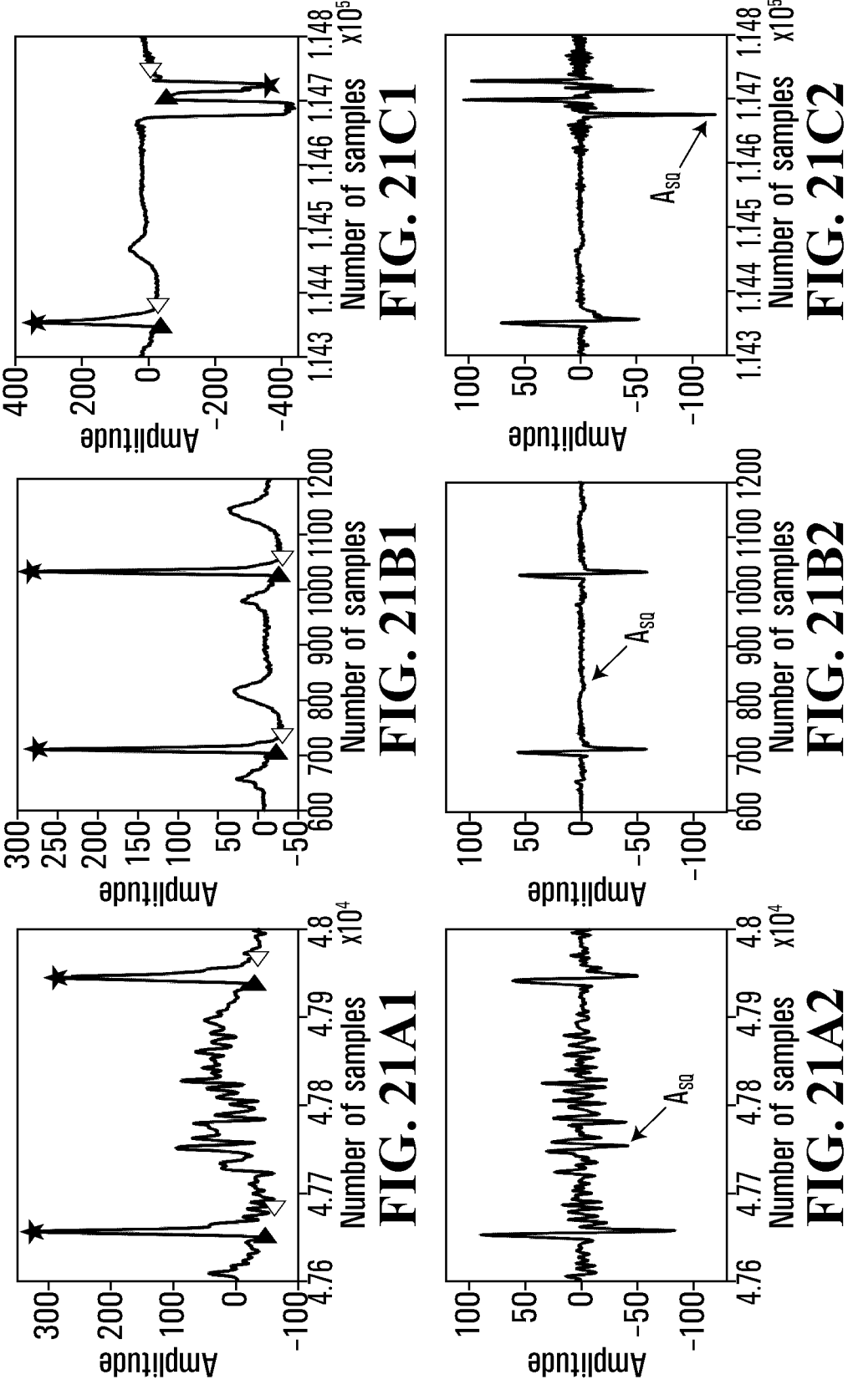

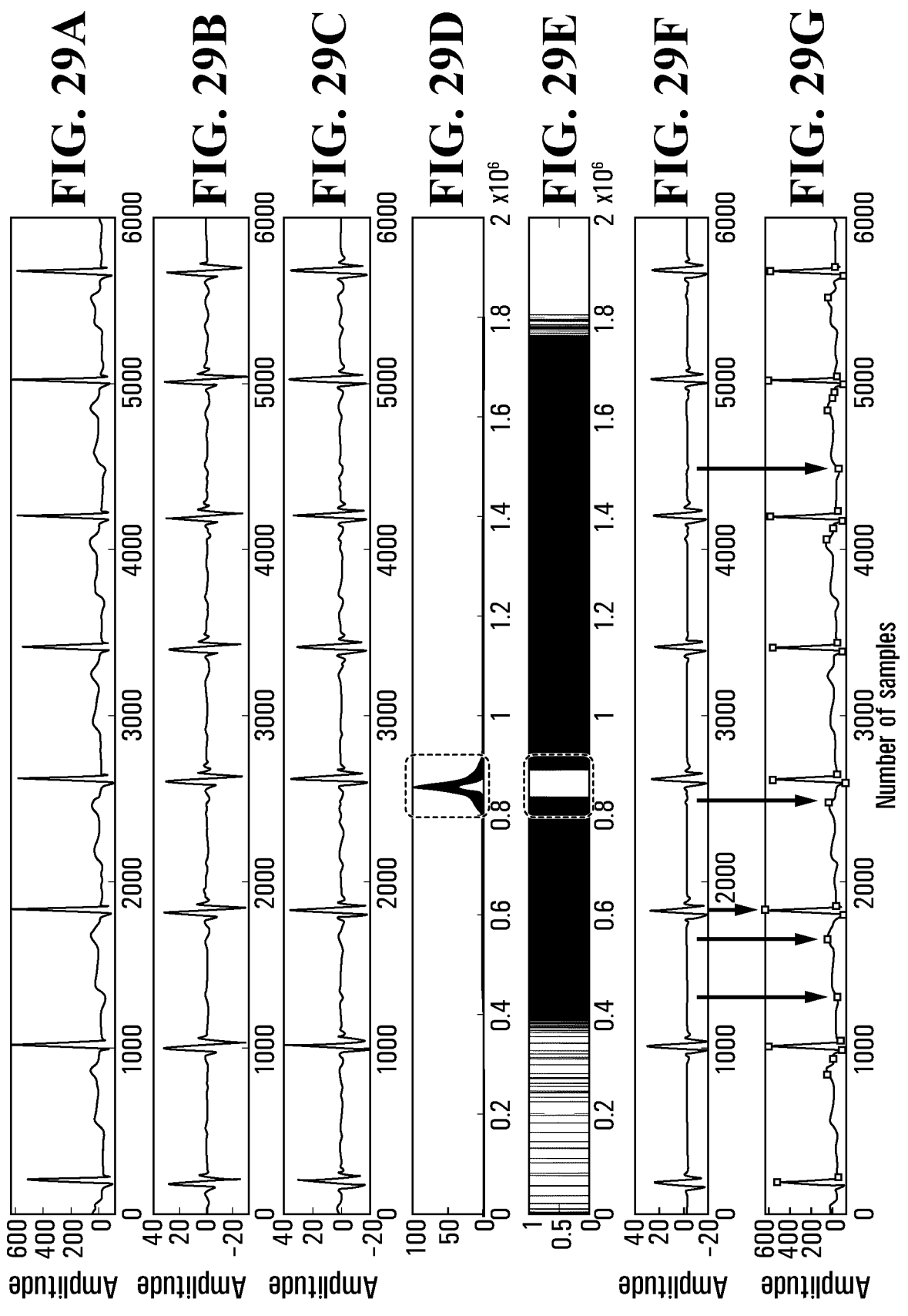

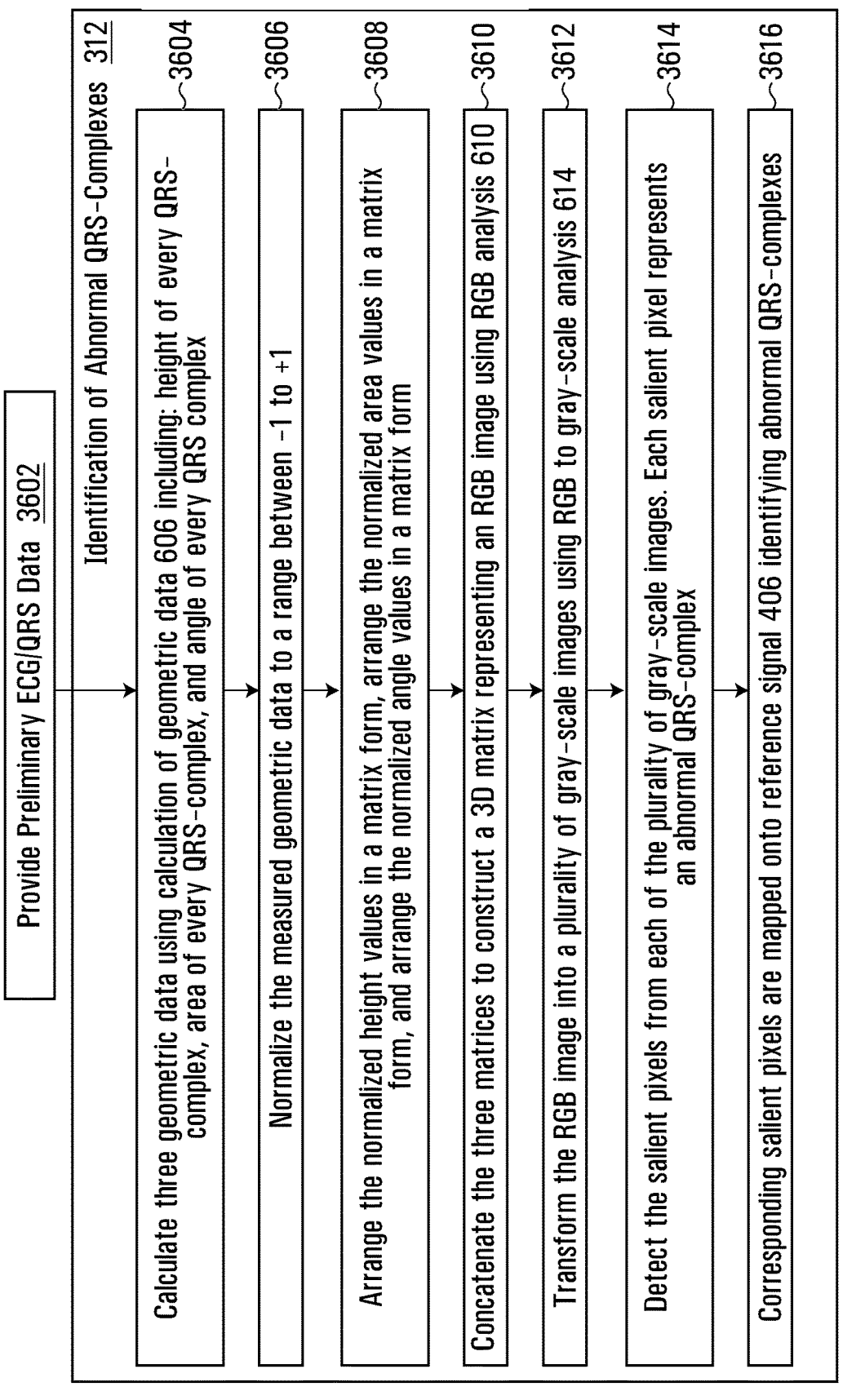

Provide Preliminary ECG/QRS Data 3602

Identification of Abnormal QRS-Complexes 312

Calculate three geometric data using calculation of geometric data 606 including: height of every QRS-complex, area of every QRS-complex, and angle of every QRS complex 3604

Normalize the measured geometric data to a range between −1 to +1 3606

Arrange the normalized height values in a matrix form, arrange the normalized area values in a matrix form, and arrange the normalized angle values in a matrix form 3608

Concatenate the three matrices to construct a 3D matrix representing an RGB image using RGB analysis 610 3610

Transform the RGB image into a plurality of gray-scale images using RGB to gray-scale analysis 614 3612

Detect the salient pixels from each of the plurality of gray-scale images. Each salient pixel represents an abnormal QRS-complex 3614

Corresponding salient pixels are mapped onto reference signal 406 identifying abnormal QRS-complexes 3616

FIG. 36

SYSTEM AND METHOD FOR SALIENCY DETECTION IN LONG-TERM ECG MONITORING

TECHNICAL FIELD

This application is a national stage application pursuant to 35 U.S.C. § 371 of PCT Application No. PCT/CA2021/050988 having an international filing date of Jul. 16, 2021, which designated the United States, and from which the PCT application claimed the benefit of U.S. Provisional Patent Application No. 63/052,826 filed Jul. 16, 2020, the entire contents of which are incorporated herein by reference. The present disclosure relates to systems and methods for automatically detecting and identifying abnormal QRS-complexes, such as in wearable electrocardiogram (ECG) monitoring devices.

BACKGROUND

Cardiovascular diseases have been a leading cause of death in North America for decades, and the occurrence of such diseases can be detected by manually analysing the electrocardiogram (ECG) signal of the heart. Specifically, through the detection of the QRS-complex in every heartbeat of the ECG signal and the identification of its normality. Manually detecting and examining every QRS-complex is cumbersome and often inaccurate.

Electrocardiogram (ECG) signals have, since their discovery, been used by medical professionals as a diagnostic tool in identifying several heart-related diseases. In particular, medical professionals examine ECG signals for abnormal QRS-complexes. A QRS-complex represents the electrical impulse that spreads though the right and left ventricles of the heart during each heartbeat, depolarization of the ventricles. A QRS-complex, hence, has three successive waves, Q, R, and S. There are also the T and U waves that succeed the S wave, respectively. An abnormal QRS-complex is one that differs from this behaviour, and could indicate the presence of various different heart diseases in the patient.

At present, in order to gather and analyze the ECG signal, medical professionals instruct patients to record their ECG signals for several hours. After that, the recorded data is examined manually in an effort to identify abnormal QRS-complexes. However, such a process has several drawbacks, most notably inefficiencies and inaccuracies.

For example, a doctor analyzing a 24 hour recording of an ECG signal would have to analyze thousands of heartbeats prior to making a determination. This results in diagnoses and treatment delays for patients and is subject to inaccuracies.

Accordingly, there exists a need to obviate or mitigate at least some of the above-mentioned disadvantages of existing systems and methods.

SUMMARY

Systems and methods for automatically and accurately identifying abnormal QRS-complex are needed to address one or more of the above mentioned shortcomings of the prior art. Thus, there remains a need for methods and systems that can reliably and efficiently identify both normal and abnormal QRS-complexes. In at least one aspect, the system and method disclosed represent heartbeats in an image through a saliency analysis process, which is advantageous as it saves a significant amount of time, improves processing speed and improves accuracy in comparison to manually examining these heartbeats. In at least some embodiments, there is provided an automated, efficient, and robust system for identifying abnormal QRS-complexes in data acquired by an ECG recording device, the method executed in the processor of the QRS-complex processing device comprising the steps of: (a) automatically identifying potential QRS-complexes by filtering the ECG input data through two zero-phase Butterworth filters; locating R-peaks through the calculation of the first-difference of the de-noised-ECG signal, then processing the data through Hilbert transform, Shannon-transform, and a histogram analysis; and locating the Q and S-peaks through pruning; (b) if motion artifact (MA) and/or sudden-change-in-baseline (SCB) noises exist, detecting and removing such noises through the calculation of the difference between two time-sample regions, in one example is consecutive regions, previously processed through a Butterworth filter; the absolute value of the maximum difference is transformed into a two-dimensional gray-scale image where its histogram is calculated, noise is located when the difference between two consecutive histogram peaks values exceeds a predefined threshold; (c) identifying abnormal QRS-complexes through utilizing QRS-complexes peaks' height, area, and angles, normalizing the geometric data and transforming them into a Red-Green-Blue (RGB) image then to multiple gray-scale images; histograms of the gray-scale images are calculated, and abnormal QRS-complex is located when the difference between two consecutive histogram peaks values exceeds a predefined threshold.

In at least some embodiments of the disclosed systems and methods for abnormal QRS-complex identification in ECG signal, the following one or more advantages may be provided:

- Automated and efficient analysis of ECG signal.
- QRS-complex detection.
- De-noising of ECG signal by automatically detecting both motion artifacts (MA) and sudden-change-in-baseline (SCB) noises.
- Identification of abnormal QRS-complexes.
- Representation of geometric measures of QRS-complexes in a single image for improved speed in processing and accurate identification of abnormal QRS-complex.
- Reduction in delays and mistakes in diagnoses and treatment by improved efficiency and accuracy of route management.

In one aspect there is provided a computer-implemented method for identifying abnormal QRS-complexes in an ECG signal using saliency detection comprising: receiving an ECG signal with detected QRS-complexes; calculating a plurality of geometric measures of the QRS-complexes comprising: QRS-angle, QRS-area, and QRS-height; normalizing the geometric measures; constructing an RGB image with three two-dimensional matrices, representing the R, G, and B planes of the RGB image, each matrix corresponds to one of the calculated plurality of geometric measures, the geometric measures belonging to one QRS-complex have the same matrix index across the three two-dimensional matrices; transforming the RGB image to a plurality of gray-scale images; computing histograms of each of the plurality of gray-scale image; iteratively comparing every histogram peak to its previous one; and marking pixel intensities corresponding to histogram peaks with a difference value of equal or greater than a predefined threshold, a saliency threshold ($Th_{int1}$), as salient pixels;

mapping salient pixels indices onto the ECG signal; and classifying respective indices on the ECG signal as abnormal QRS complexes.

In another aspect, there is provided a computer-implemented method for detecting motion artifact and sudden-change-in-baseline using saliency detection in ECG signals comprising: receiving an ECG signal with pre-located QRS-complexes; computing the absolute maximum amplitude of the first difference of every region between an S-peak of a QRS-complex and a Q-peak of the consecutive QRS-complex, SQ regions; normalizing the absolute maximum amplitudes of the SQ regions; arranging in a matrix form constructing a gray-scale image; computing histogram of the gray-scale image; iteratively comparing every histogram peak to its previous one; and calculating salient intensities corresponding to histogram peaks with a difference value of more than a predefined threshold; mapping salient intensities indices onto the ECG signal; and classifying respective indices on the ECG signal as noise.

In another aspect, there is provided a computer-implemented method for identifying abnormal QRS-complexes in an ECG signal using saliency detection comprising: receiving an ECG signal with pre-located QRS-complexes; arranging each type of geometric measures from the QRS-complexes in a three dimensional matrix, the geometric measures belonging to a QRS-complex have the same index across the three dimensional matrix, constructing an RGB image; transforming the RGB image to a plurality of gray-scale images; computing histograms of each of the plurality of gray-scale image; iteratively comparing every histogram peak to its previous one; and calculating salient intensities corresponding to histogram peaks with a difference value of more than a predefined threshold; mapping salient intensities indices onto the ECG signal; and classifying respective indices on the ECG signal as abnormal QRS complexes.

In another aspect, there is provided a computer program product comprising a non-transient storage device comprising instructions that when executed by at least one processor a computing device, configure the computing device for identifying abnormal QRS-complexes in an ECG signal using saliency detection comprising and configure the computing device to: receive an ECG signal with detected QRS-complexes; calculate a plurality of geometric measures of the QRS-complexes comprising: QRS-angle, QRS-area, and QRS-height; normalize the geometric measures; construct an RGB image with three two-dimensional matrices, representing the R, G, and B planes of the RGB image, each matrix corresponds to one of the calculated plurality of geometric measures, the geometric measures belonging to one QRS-complex have the same matrix index across the three two-dimensional matrices; transform the RGB image to a plurality of gray-scale images; compute histograms of each of the plurality of gray-scale image; iteratively comparing every histogram peak to its previous one; and mark pixel intensities corresponding to histogram peaks with a difference value of equal or greater than a predefined threshold, a saliency threshold $(Th_{int1})$, as salient pixels; map salient pixels indices onto the ECG signal; and classify respective indices on the ECG signal as abnormal QRS complexes.

In another aspect, there is provided a computing device comprising a processor, a non-transient storage device and a communication device where each of the storage device and the communication device is coupled to the processor, the storage device storing instructions that when executed by the processor, configure the computing device to: receive an ECG signal with detected QRS-complexes; calculate a plurality of geometric measures of the QRS-complexes comprising: QRS-angle, QRS-area, and QRS-height; normalize the geometric measures; construct an RGB image with three two-dimensional matrices, representing the R, G, and B planes of the RGB image, each matrix corresponds to one of the calculated plurality of geometric measures, the geometric measures belonging to one QRS-complex have the same matrix index across the three two-dimensional matrices; transform the RGB image to a plurality of gray-scale images; compute histograms of each of the plurality of gray-scale image; iteratively comparing every histogram peak to its previous one; and mark pixel intensities corresponding to histogram peaks with a difference value of equal or greater than a predefined threshold, a saliency threshold $(Th_{int1})$, as salient pixels; map salient pixels indices onto the ECG signal; and classify respective indices on the ECG signal as abnormal QRS complexes.

BRIEF DESCRIPTION OF THE DRAWINGS

These and other features of the invention will become more apparent from the following description in which reference is made to the appended drawings wherein:

FIG. 8 is a flowchart showing example operations of the histogram analysis of the ECG signal of FIG. 4 for the computing system environment of FIG. 1 and the processing device of FIG. 2, in accordance with an embodiment.

FIG. 9 is a flowchart showing example operations of the pruning of non-QRS-complexes of FIG. 4 for the computing system of FIGS. 1 and 2, in accordance with an embodiment.

FIG. 11 is a flowchart showing example operations of the saliency analysis used in the removal of residual noise from the preliminary ECG/QRS data as shown in FIG. 5, in accordance with an embodiment.

FIGS. 15A and 15B illustrate example graphs of the processing of data that occurs in the first difference stage shown in FIG. 4 in accordance with an embodiment.

FIGS. 21A1, B1, C1, A2, B2, and C2 illustrate example graphs of the identification of the maximum amplitude in first difference data in the removal of residual noise from the ECG signal stage shown in FIG. 5 in accordance with an embodiment.

FIG. 22A illustrates an initial histogram featuring peaks in the intensity value. FIG. 22B illustrates a calculation of the intensity difference between peaks. FIG. 22C illustrates an identification of a second peak #2 whose intensity difference with peak #1 is equal or greater than the saliency threshold. FIG. 22D illustrates the removal of peak 2 prior to reiteration of histogram analysis.

FIGS. 23A and B illustrate the geometric data calculated in the identification of abnormal QRS-complexes stage seen in FIG. 6 in accordance with an embodiment. FIGS. 23A and 23B illustrate a visual representation of the geometric data 608 identified in the calculation of geometric data.

FIG. 25 illustrates an ECG signal and the right hand side FIG. 25 illustrates an RGB image of the normalized feature values.

FIGS. 29A-G illustrate example graphs showing the series of transformations of the input ECG signal for the detection of peaks in the original input ECG signal in accordance with an embodiment.

FIG. 31 illustrates an example saliency analysis to identify abnormal QRS-complex, in accordance with an embodiment.

FIG. 32 illustrates an example saliency analysis to identify abnormal QRS-complex, in accordance with an embodiment.

FIG. 35A illustrates abnormal QRS complex identification using visual representation of multiple QRS complexes with saliency analysis and FIG. 35B illustrates abnormal QRS complex identification using time domain ECG signal.

FIG. 36 shows a flowchart presenting an overview of saliency analysis for identifying abnormal QRS-complexes, in accordance with an embodiment in accordance with an embodiment.

While references to "an embodiment" are used herein, nothing should be implied or understood that features of one embodiment cannot be used or combined with features of another embodiment unless otherwise stated. The various systems, methods and devices shown and described herein may be used together unless otherwise stated.

DETAILED DESCRIPTION

Reference will now be made in details to embodiments of the present disclosure, examples of which are illustrated in the accompanying drawings. Wherever possible, the same reference numbers will be used throughout the drawings to refer to the same or like parts.

In at least some embodiments, the present disclosure discloses an automated system and method for detecting QRS complexes. In at least some embodiments, there is disclosed a system and method for identification of abnormal QRS-complexes. The process includes using saliency analysis to identify abnormal QRS-complexes in data acquired by an ECG recording device. Saliency analysis can also be used to identify motion artifact (MA) and sudden-change-in-baseline (SCB) noises. Each individual electronic recording device (such as a wearable ECG monitoring device) sends its raw ECG signal to the QRS processing device through a communications network. The automated systems and methods in the QRS processing device then automatically identifies abnormal QRS-complexes. Further preferably, in at least some embodiments, the processed ECG signal and detected QRS-complexes are then sent to a central server, such as the client monitoring device for subsequent diagnoses and analysis.

Saliency analysis according to one or more embodiments of the present disclosure includes extracting data from QRS-complexes of ECG signal and representing them as an image, an RGB image for identifying abnormal QRS-complexes, and a gray scale image for identifying MA and SCB noises. This process transforms an ECG signal with QRS-complexes to a single image. Each pixel of the image corresponds to a specific QRS-complex in the ECG signal. Histogram analysis is performed on the image to compare histogram peaks. When the difference between two consecutive peak values exceeds a predefined threshold, also referred to as the saliency threshold ($Th_{int}$), the histogram peak with higher intensity value corresponds to salient pixel. These salient pixels belong to abnormal QRS-complexes or MA and SCB noises, depending on the type of data used to represent the image.

Figure 1:
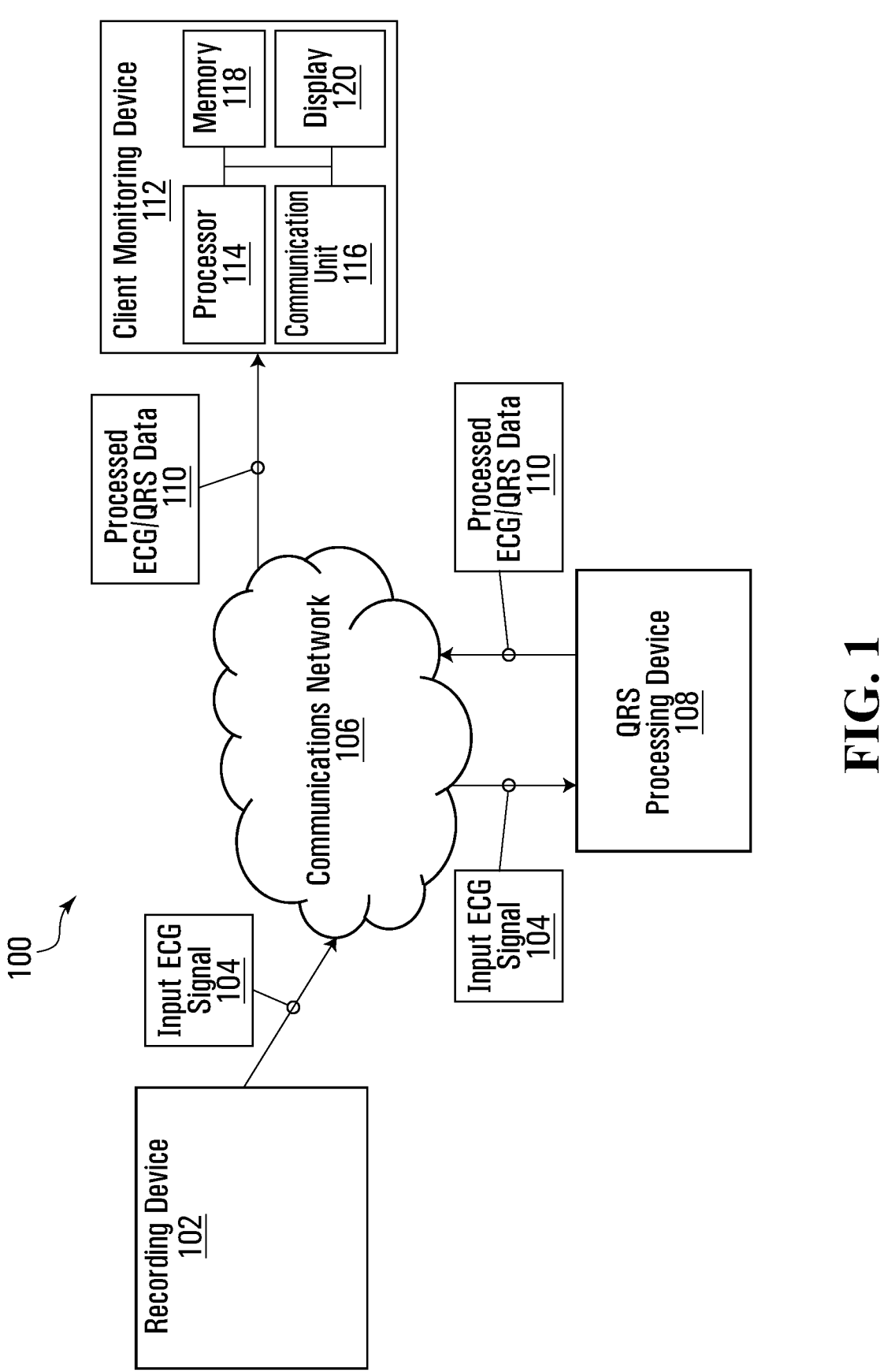
FIG. 1 is a schematic block diagram of a QRS computing system environment for providing automated identification of abnormal QRS-complexes in ECG signal, in accordance with an embodiment.

Referring to FIG. 1, shown is a block schematic diagram of a computing environment 100 for identifying abnormal QRS-complexes in an ECG signal. It provides automated QRS-complex detection to data acquired by an ECG electronic capturing device, also referred to as a recording device 102. The recording device 102 communicates with the QRS processing device 108. The QRS processing device 108 communicates with a central monitoring device or server such as a client monitoring device 112, in at least some embodiments. In other embodiments, the QRS processing device 108 can include the client monitoring device 112 as part of the functionality of the QRS device 108 and thus communicates internally with such device.

The QRS processing device 108 detects QRS-complexes and identifies abnormal QRS-complexes. It receives as input, an input ECG signal 104, from the recording device via the communications network 106. The QRS processing device 108 preprocesses the input ECG signal 104 generating a preprocessed signal and keeping a reference signal. The QRS processing device 108 enhances the QRS-complexes regions and suppresses low frequency components by calculating the first difference of the preprocessed signal. R-peaks have a value of zero and become inflexion-points after calculating the first difference. Hilbert transform switches its polarity if there is an inflexion-point; therefore, applying it to the first difference reveals plausible peaks, R-peaks of the QRS-complexes in particular. Shannon energy transform is also applied to further enhance the plausible R-peaks due to its characteristic of having positive monotonicity. Further, histogram analysis is applied to ablate samples not belonging to QRS-complexes, reducing the number of falsely detected R-peaks and preserving potential R-peaks. The potential R-peaks are mapped onto the reference signal and the S and Q-peaks are detected. The three peaks represent the QRS-complexes of the input ECG signal.

The process of saliency analysis according to one or more embodiments includes representing selected data of QRS-complexes of heartbeats as an image, allowing for accurate and faster processing of abnormal QRS-complexes and MA and SCB noise identification using a visual representation. Saliency analysis is performed by transforming data into a gray-scale image and then calculating the histogram of the gray-scale image. If the difference between a histogram peak and its previous peak exceeds a predefined threshold, e.g. $Th_{int}$, then that histogram peak corresponds to an undesired data, whether it is MA and SCB noise or abnormal QRS-complexes.

Saliency threshold, $Th_{int}$ value for abnormal QRS-complex identification could be different than $Th_{int}$ value for MA and SCB noise identification. Therefore, in at least some embodiments, this disclosure refers to $Th_{int}$ for abnormal QRS-complex identification as $Th_{int1}$ and for MA and SCB noise identification as $Th_{int2}$.

Figures 35A, 35B:
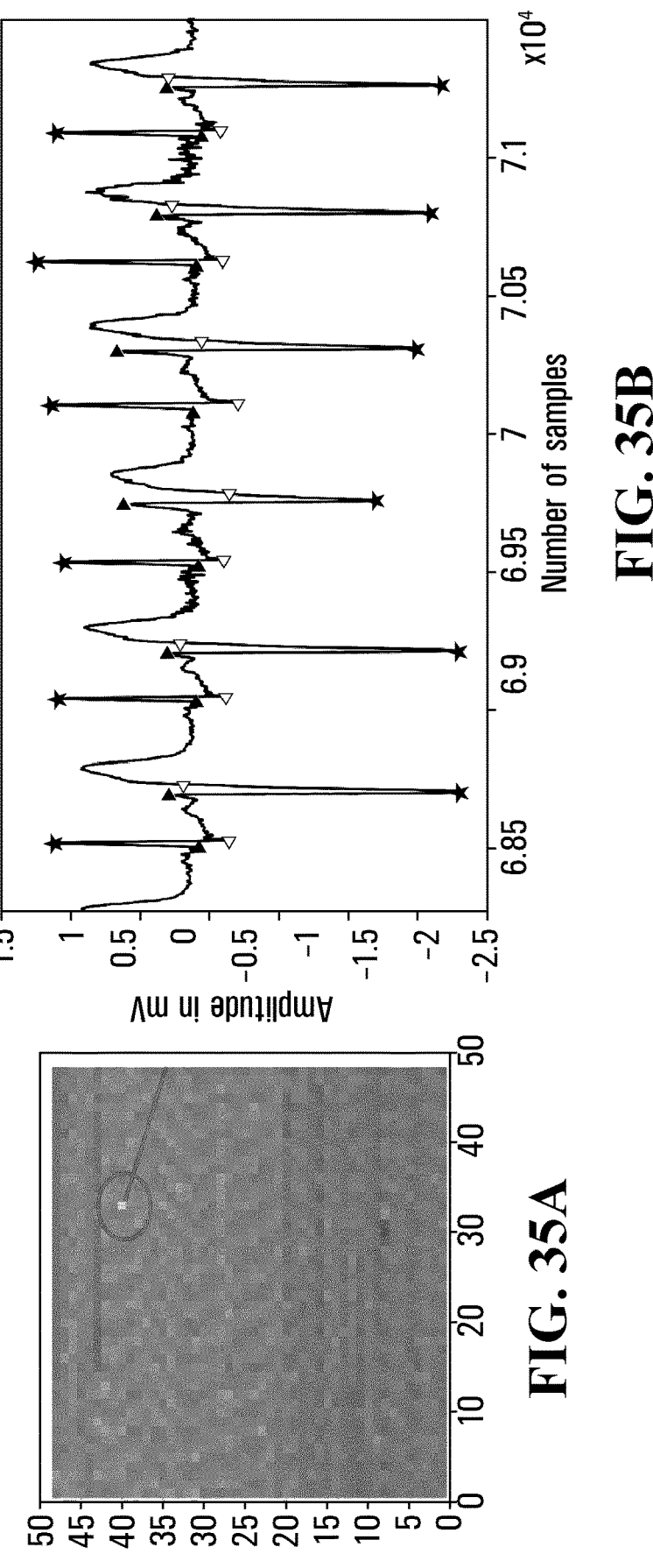
FIGS. 35A-B illustrate example graphs comparing identification of abnormal QRS-complexes using visual representation of QRS-complexes through the process of saliency analysis (FIG. 35A) in comparison to the same task using time ECG signal (FIG. 35B) in accordance with an embodiment. For example.

The data of MA and SCB noise correspond to the regions between two consecutive QRS-complexes, and the data of abnormal QRS-complexes correspond to geometric measures of the QRS-complexes. FIGS. 35A-B show a schematic of abnormal QRS-complex identification by examining QRS-complexes represented as a single image using saliency analysis (FIG. 35A) in contrast to manually examining abnormal QRS-complexes in time domain ECG signal (FIG. 35B).

Communication between the recording device 102, the QRS processing device 108, and the client monitoring device 112 occurs via a computer implemented communications network 106, including, for example, Dedicated Short Range Communication (DSRC), Long-Term Evolution (LTE), 5G, across a network such as the Internet or other well-known communication standards.

Referring to FIG. 1, the communicating network of the recording device 102 with the QRS processing device 108 and the client monitoring device 112 allows for automated processing of an input ECG signal 104 into a processed ECG/QRS data 110. The QRS processing device 108 is configured for automatically identifying residual noise (MA and SCB noise) and abnormal QRS-complexes.

Referring again to FIG. 1, the following provides example computer implementations of each of the recording device 102, QRS processing device 108, and client monitoring device 112.

Referring to recording devices 102, examples can include but are not limited to: a Holter ECG recording or a wearable ECG device. The recording device 102 communicates the captured ECG signal as input ECG signal 104 to the QRS processing device 108 through a communications network 106, including, for example, Dedicated Short Range Communication (DSRC), Long-Term Evolution (LTE), 5G, and across a network such as the Internet or other well-known communication standards.

Referring to the client monitoring device 112 shown in FIG. 1, an example of a client monitoring device 112 is a computing device (e.g. a portable computer, a personal computer) as shown in FIG. 1, and can include: a processor 114, a memory 118, a communication unit 116, and a display 120. The communication unit 116 and the processor 114 are calibrated to communicate with the communications network 106, through which the client monitoring device 112 receives the processed ECG/QRS data 110 from the QRS processing device 108. The memory 118 is configured to store the processed ECG/QRS data 110 for subsequent analysis or access. When called upon, processor 114 sends request to fetch the processed ECG/QRS data 110 and present it on the display 120.

Referring to the QRS processing device 108, an example of a QRS processing device 108 is a computing device (e.g. a portable computer, a personal computer) as shown in FIG. 1.

Figure 2:
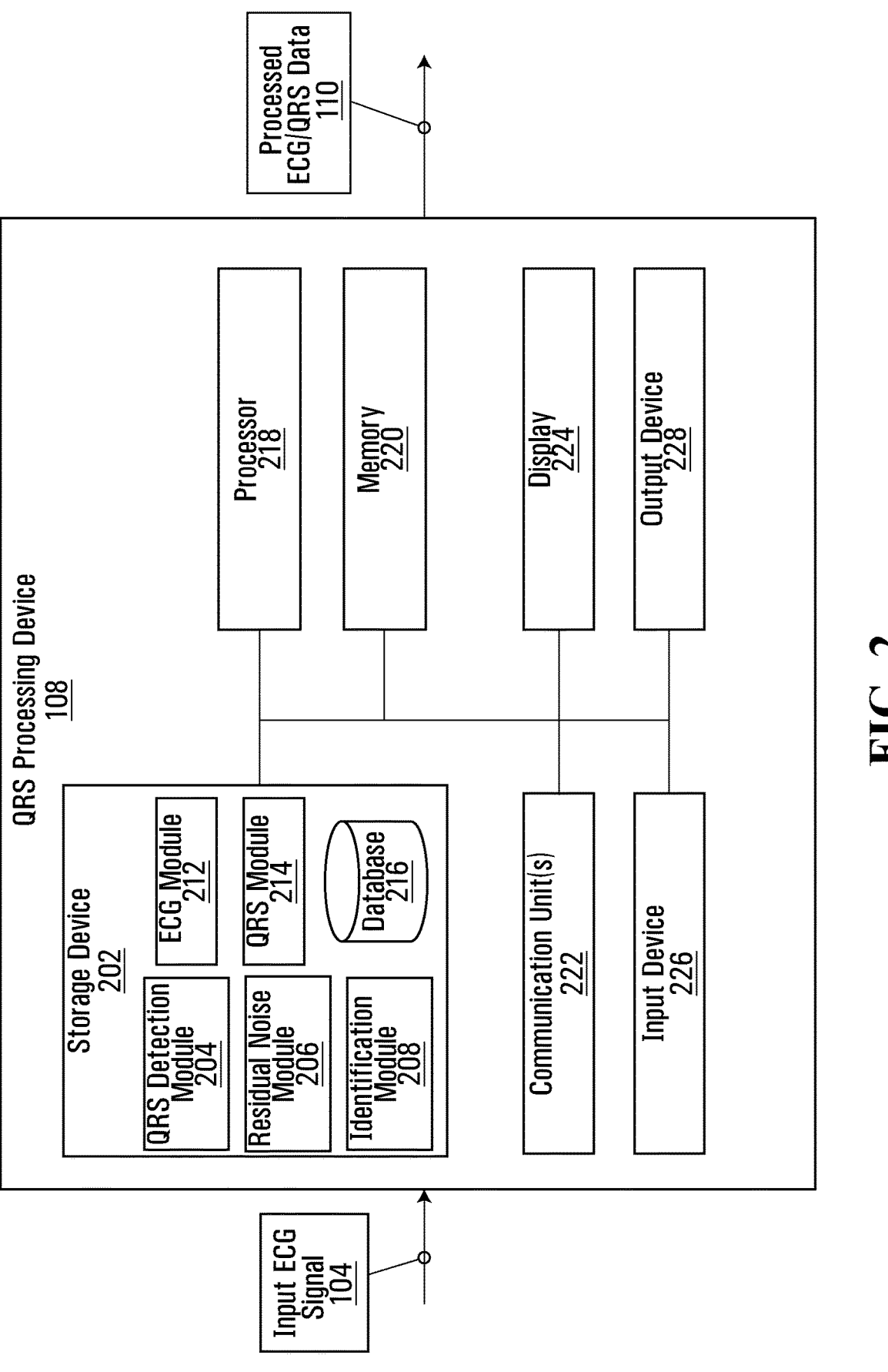
FIG. 2 is a schematic block diagram of a QRS-complex processing device of FIG. 1, in accordance with an embodiment.

Referring to FIG. 2, shown is a schematic of the computing components of the QRS processing device 108. Referring now to FIGS. 1 and 2, the QRS processing device 108 can include: a storage device 202, a processor 218, a memory 220, communication unit(s) 222, a display 224, an input device 226, and an output device 228. The communication unit(s) 222 and the processor 218 are calibrated to communicate, using the input 226 and output 228 devices, with the recording device(s) 102 and the client monitoring device(s) 112 via the communications network 106, receiving the input ECG signal 104 from the recording device 102, and sending the processed ECG/QRS data 110 for subsequent processing such as via the client monitoring device 112. The memory 220 stores the input ECG signal 104 the processed ECG/QRS data 110 and other data as discussed in relation to FIGS. 3-6. In some aspects, the storage device 202 contains the database 216, QRS detection module 204, residual noise module 206, identification module 208, ECG module 212, and QRS module 214. Upon receiving a trigger for QRS analysis, the processor 218 uses the ECG module 212 to obtain the input ECG signal 104 from the memory 220 (e.g. a previously captured ECG signal). The processor 218 then applies the input ECG signal 104 to the QRS detection module 204, residual noise module 206, and identification module 208, using the example steps shown in FIGS. 3-11. In some aspects, the processor 218 may store the processed ECG/QRS data 110 in the memory 220 and/or database 216 using the QRS module 214. In some aspects, stored in the memory 220 is a database 216 of the input ECG signal 104, processed ECG/QRS data 110, and other data as discussed in relation of FIGS. 3-6. Finally, the processor 218 takes the processed ECG/QRS data 110 (e.g. as may be stored in the memory 220 or otherwise accessible to the processor 218) and sends it through the communications network 106 to the client monitoring device 112 via the output device 228 and the communications unit(s) 222, for subsequent review, reporting and/or analysis. As can be understood by a person skilled in the art, the processor 218 can call any data in the memory 220 and present it to a user on the display 224.

Figure 3:
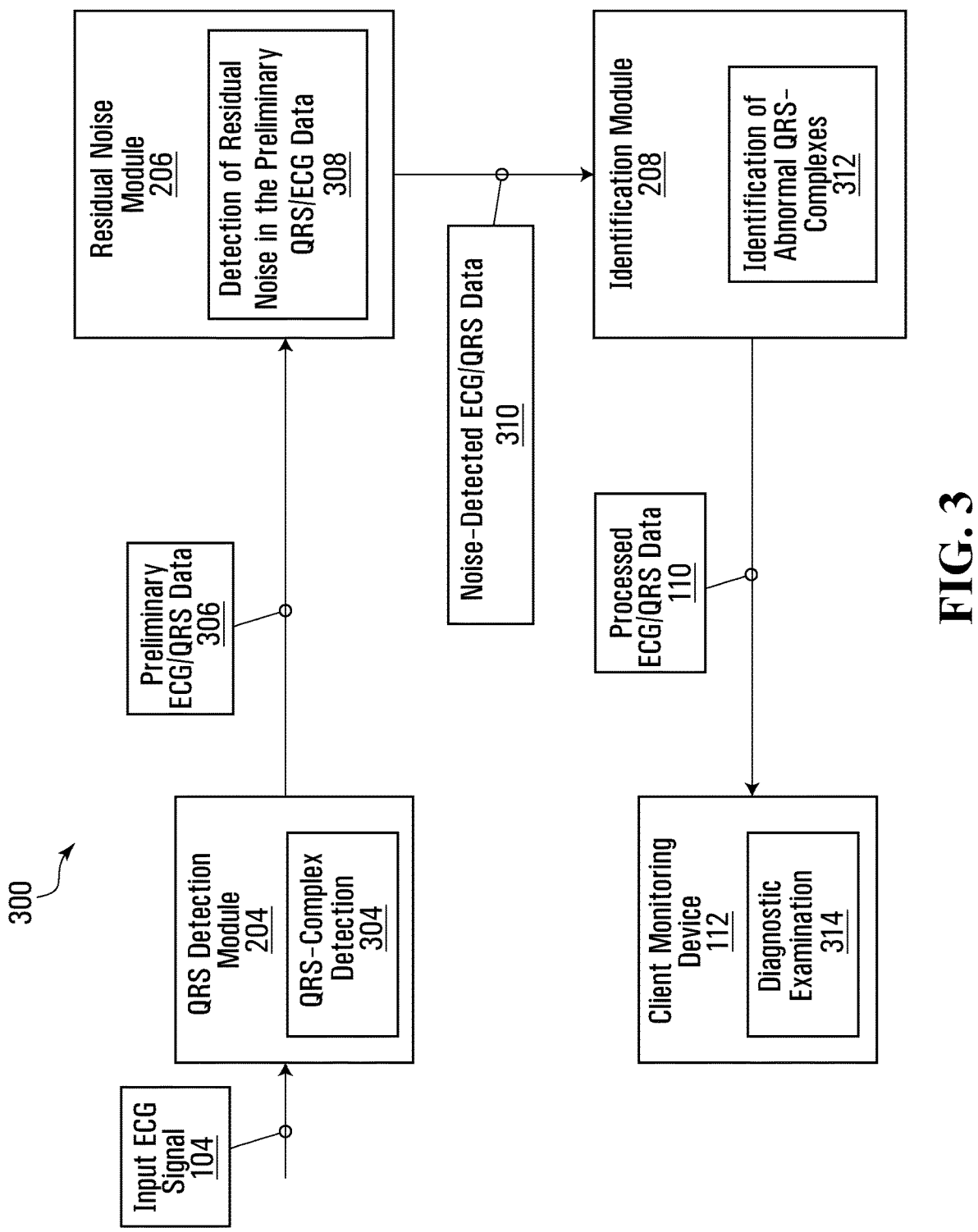
FIG. 3 is a flowchart showing the operations of abnormal QRS-complex detection from raw ECG signal input for the computing system environment of FIG. 1 and the processing device of FIG. 2, in accordance with an embodiment.

Referring to FIG. 3, shown is a flowchart of a computing environment 300 of operation, according to an embodiment where the input ECG signal 104 is filtered into processed ECG/QRS data 110 in the QRS processing device 108 for output on the client monitoring device 112. At the QRS-complex detection 304 step, the input ECG signal 104 is run through the QRS detection module 204, creating preliminary ECG/QRS data 306, which contains the detected QRS-complexes, that is sent by the processor 218 to the memory 220. The processor 218 then sends the preliminary ECG/QRS data 306 for detection of residual noise in the preliminary ECG/QRS data 308 in the residual noise module 206. The result is the noise-detected ECG/QRS data 310 which is then sent by the processor 218 to the memory 220. The processor 218 then applies the noise-detected ECG/QRS data 310 into the identification module 208 for the identification of abnormal QRS-complexes 312, creating the processed ECG/QRS data 110, which is sent by the processor 218 to the memory 220. The processed ECG/QRS data 110 is then sent by the processor 218 to the client monitoring device 112 for diagnostic examination 314 of the abnormal QRS-complexes.

Figure 4:
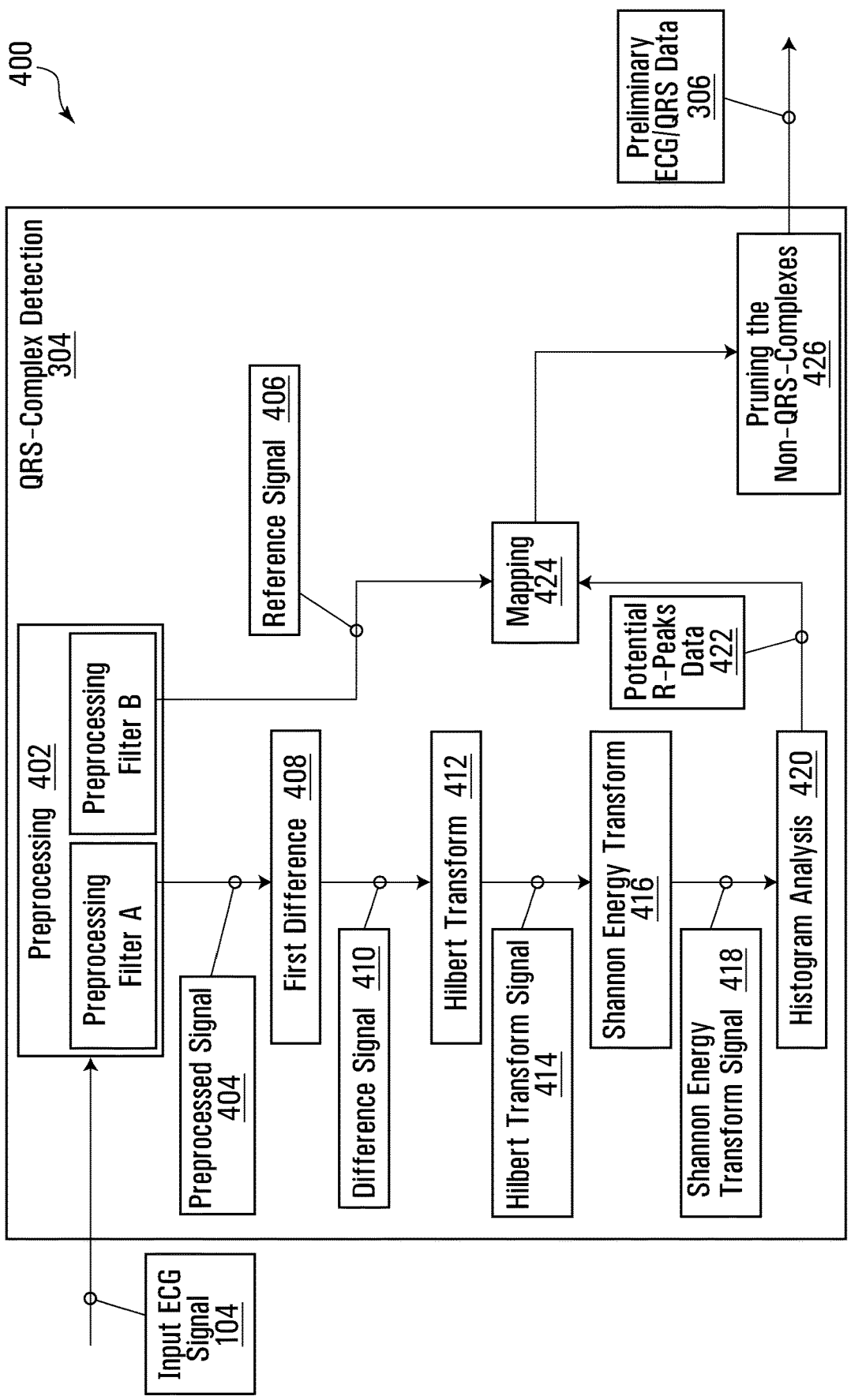
FIG. 4 is a flowchart showing example operations of the initial QRS-complex detection phase as shown in FIG. 3, in accordance with an embodiment.

Referring to FIG. 4, shown is a flow diagram of the steps 400 taken in the QRS-complex detection 304 of FIG. 3. Initially, the input ECG signal 104 is filtered to reduce noise and aid in QRS-complex detection in the preprocessing stage 402 which is detailed further in FIG. 7.

Figure 7:
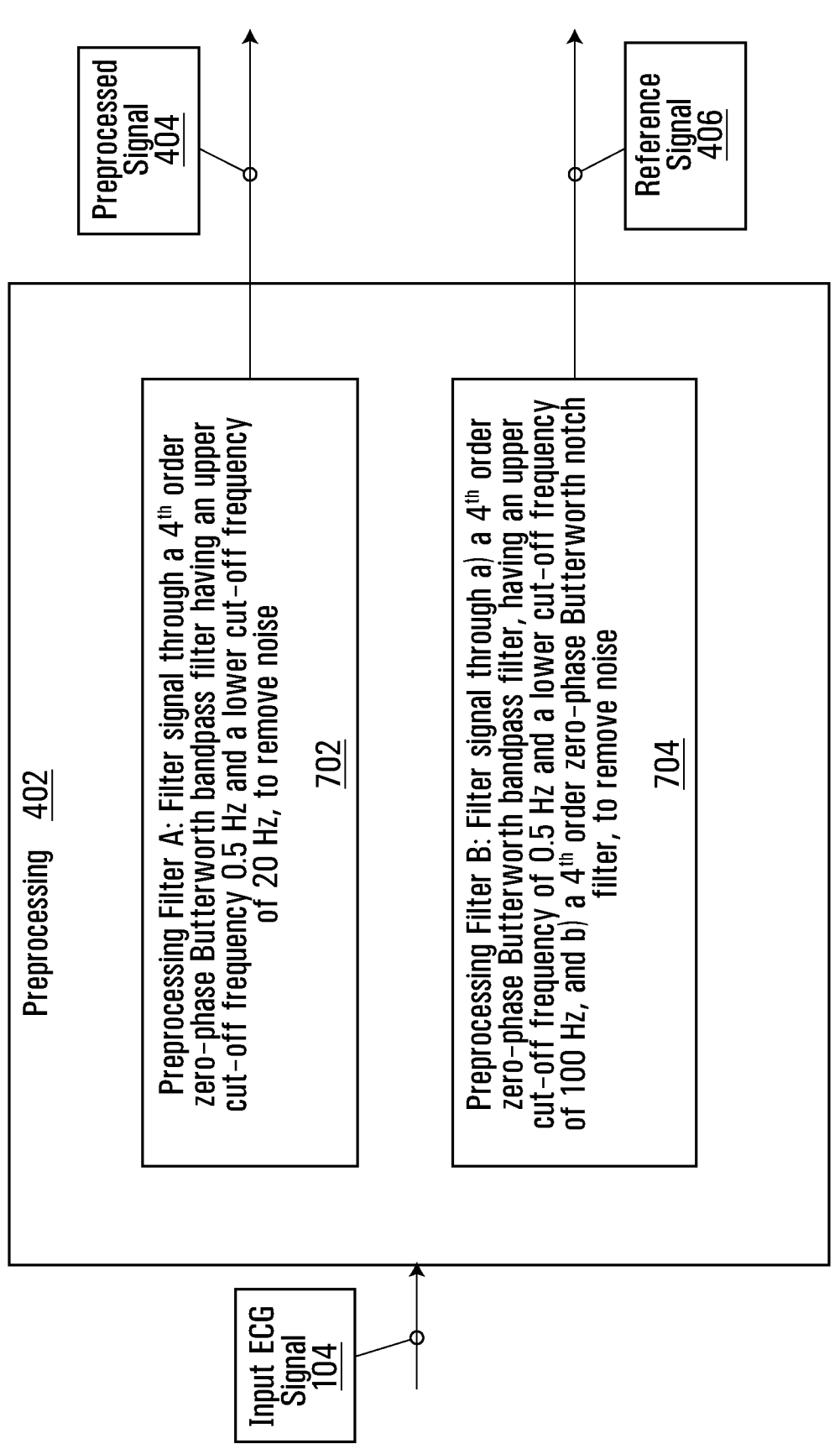
FIG. 7 is a flowchart showing example operations of the preprocessing of the ECG signal of FIG. 4 for the computing system environment of FIG. 1 and processing device of FIG. 2, in accordance with an embodiment.

Referring to FIG. 7, shown is a flow diagram, according to an embodiment, of the filters applied in the preprocessing stage 402 (e.g. see FIG. 4) that creates two independent filtered signals: the preprocessed signal 404 and the reference signal 406. The preprocessed signal 404 is generated by preprocessing filter A 702 which involves processing the input ECG signal 104 through a $4^{th}$ order zero-phase Butterworth bandpass filter having a lower cut-off frequency of 0.5 Hz, and an upper cut-off frequency of 20 Hz to remove noise.

The reference signal 406 is generated by preprocessing filter B 704 which involves separately filtering the input ECG signal 104 through a) a $4^{th}$ order zero-phase Butterworth bandpass filter having a lower cut-off frequency of 0.5 Hz, and an upper cut-off frequency of 100 Hz, and b) a $4^{th}$ order zero-phase Butterworth notch filter to remove noise.

In at least one embodiment, the reference signal 406 is the ECG signal with no filtration applied, e.g. the original ECG signal.

Figures 14A, 14B:
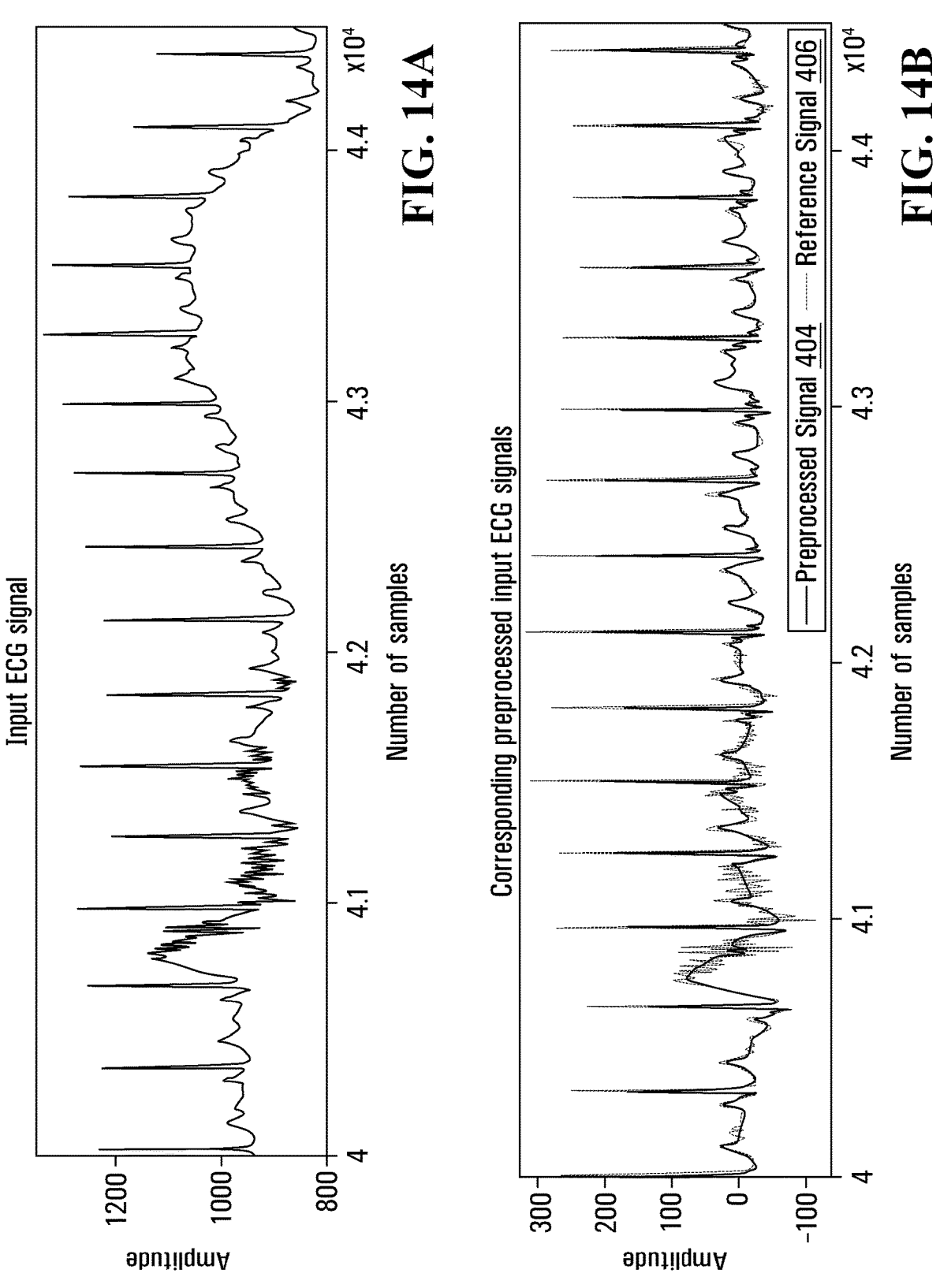
FIGS. 14A and 14B illustrate example graphs of the processing of data that occurs in the preprocessing stage shown in FIGS. 4 and 7 in accordance with an embodiment.

Both the preprocessed signal 404 and the reference signal 406 are further processed or used in subsequent steps in QRS-complex detection 304. FIGS. 14A-14B show, as an example, the preprocessing of the input ECG signal 104 (FIG. 14A) to separately generate the preprocessed signal 404 and the reference signal 406 (FIG. 14B).

Referring back to FIG. 4, the preprocessed signal 404 is, in one embodiment, subsequently transformed to the difference signal 410 by calculating the first difference 408, as follows:

$$FD(i-1) = ECG_{D20}(i) - ECG_{D20}(i-1) \qquad (1)$$

Where $ECG_{D20}$ is the preprocessed signal 404, i equals 2, 3, 4, . . . , N, and N is the length of the preprocessed signal 404 (total number of data points). FD is the first difference signal 410, and $ECG_{D20}$ refers to data points within the preprocessed signal 404. The difference signal 410 enables the QRS0-complexes of the ECG signal to be more easily located. FIGS. 15A-15B show, as an example, a preprocessed signal 404 shown in FIG. 15A that has been transformed to a difference signal 410 in FIG. 15B.

The first difference 408 is calculated in order to enhance the QRS-complex regions and to suppress the amplitudes of the low-frequency components. Benefits to this are that the QRS-complex regions become enhanced by taking the first difference and that the R-peak, or the tip of the QRS-complex is identified by 'zero' value after taking the first difference. An example of the results from this stage can be seen in FIG. 15B.

Referring again to FIG. 4, the difference signal 410 is subsequently Hilbert transformed at step 412 to provide the Hilbert transform signal 414 as output. The Hilbert transformation 412 of the difference signal 410 is computed by:

$$H_{FD}(t) = FD(t) * \frac{1}{\pi t} = \frac{1}{\pi t} \int_{-\infty}^{\infty} \frac{FD(\tau)}{t-\tau} d\tau = \frac{1}{\pi} \int_{-\infty}^{\infty} \frac{FD(t-\tau)}{\tau} d\tau$$

Where $H_{FD}(t)$ is the Hilbert transform signal 414.

Figures 16A, 16B:
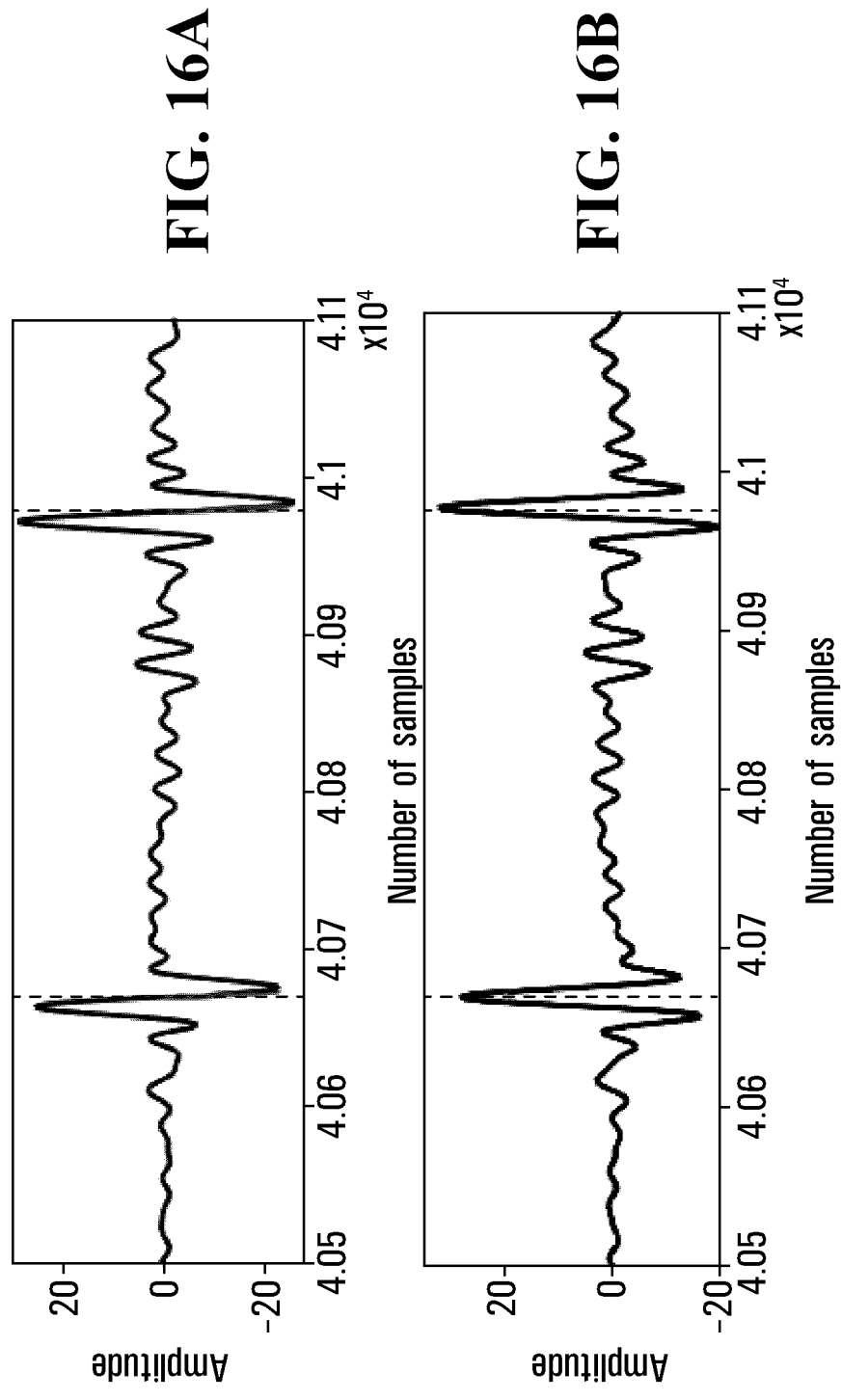
FIGS. 16A and 16B illustrate example graphs of the processing of data that occurs in the Hilbert transform stage seen in FIG. 4 in accordance with an embodiment.

The transformation to the Hilbert transform signal 414 will result in crossing the zero-line on the x-axis every time there is an inflexion point in the input ECG signal 104. This allows for better identification of the potential QRS-complex. Consequently, a zero-crossing event in a sequence of Hilbert transform signals 414 between two consecutive positive and negative points denotes a peak in the input ECG signal 104. FIGS. 16A and 16B show, as example, a difference signal 410 (FIG. 16A) that has been transformed to a Hilbert transform signal 414, such as via Hilbert transform 412 process (FIG. 16B).

Referring back to FIG. 4, the Hilbert transform signal 414 is subsequently transformed to the Shannon energy transform signal 418 by the Shannon energy transform step 416, which is a non-linear transformation having the characteristics of positive monotonicity. The Shannon energy transform step 416 is calculated using the following equation:

$$SH(i) = -(H_{FD}(i))^2 \times \log (H_{FD}(i))^2$$

Where i equals 1, 2, 3, . . . , N, and SH(i) is the Shannon energy transform signal 418 of the Hilbert transform signal 414.

Figures 17A, 17B:
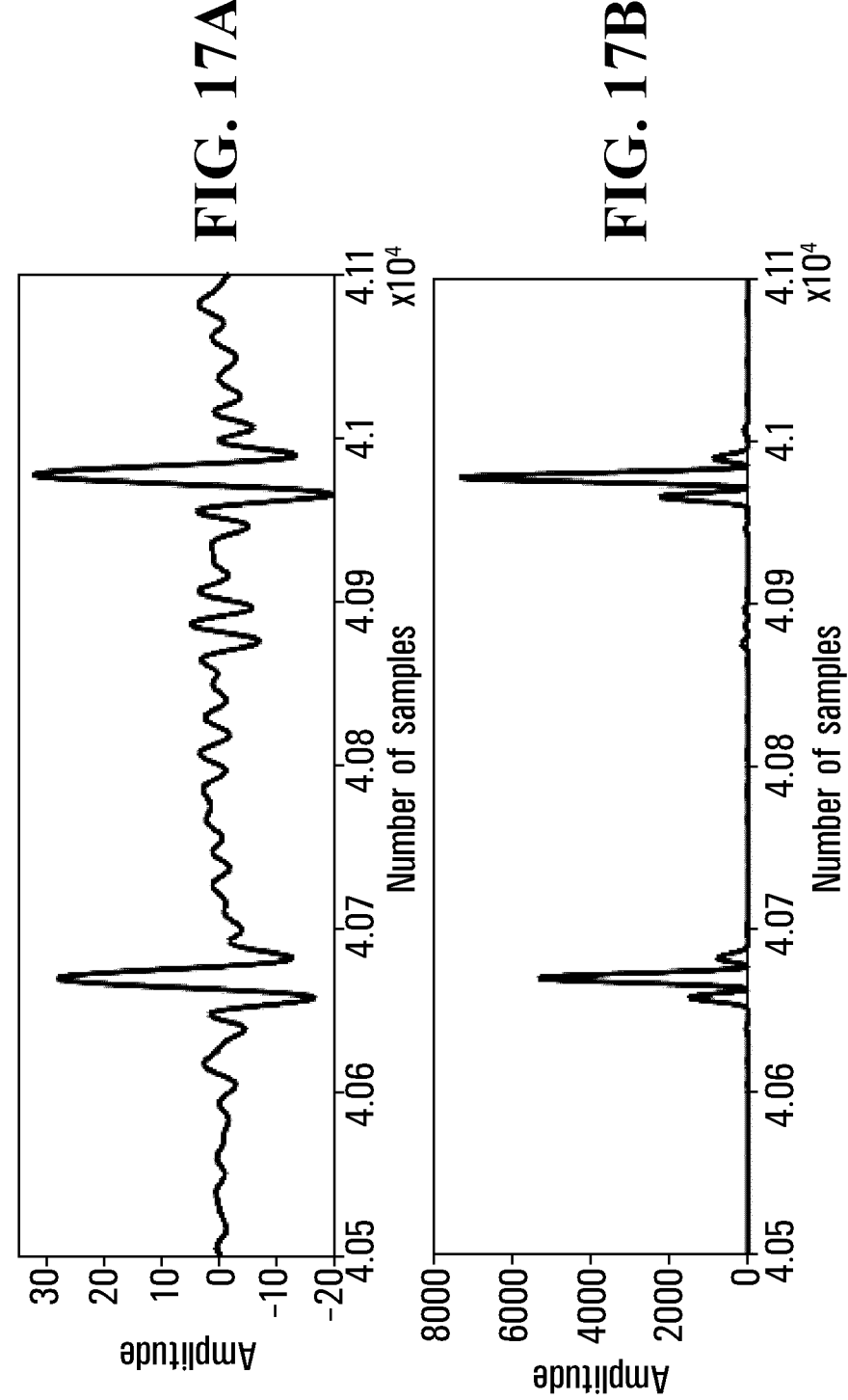
FIGS. 17A and 17B illustrate example graphs of the processing that occurs in the Shannon energy transform stage seen in FIG. 4 in accordance with an embodiment.

The Shannon energy transformation helps with the identification of QRS-complexes even under noisy conditions by non-linearly amplifying higher amplitudes while suppressing signals with lower amplitudes. FIG. 17A-B show, as an example, a Hilbert transform signal 414 (FIG. 17A) transformed to the Shannon energy transform signal 418 transformed via Shannon energy transformation 416.

Referring back to FIG. 4, after applying the Shannon energy transformation and deriving the Shannon energy transform signal 418 at step 416, the processor 218 is configured to apply a histogram analysis at step 420 in order to minimize the possibility of false QRS detection by reducing the low-frequency non-QRS components.

Figure 19:
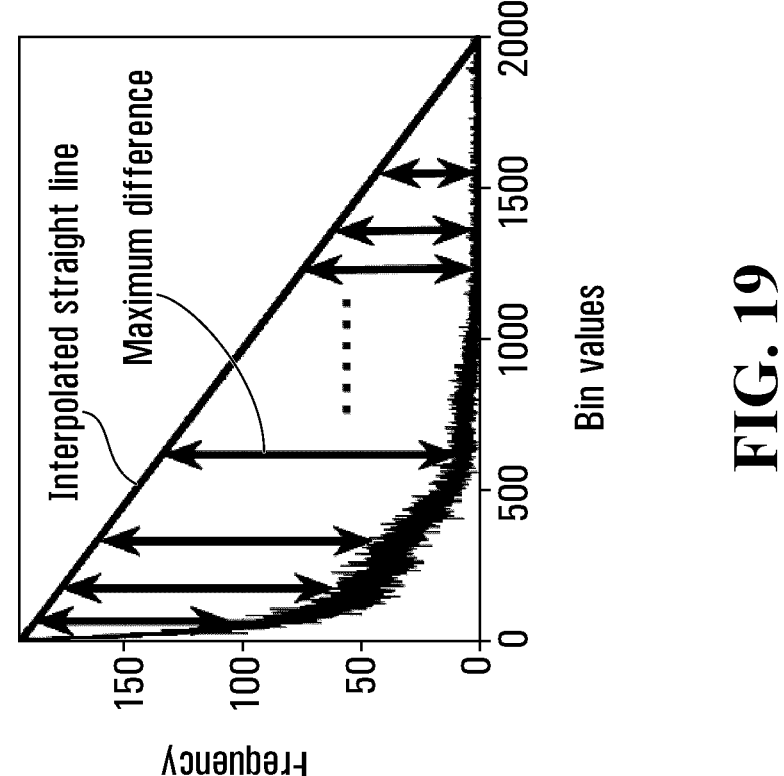
FIG. 19 illustrates an example graph of the use of linear interpolation in FIGS. 4 and 8 in accordance with an embodiment.

FIG. 8 illustrates an example flowchart of the histogram analysis 420, according to an embodiment. First, the amplitude values of the Shannon energy transform signals 418 are converted to histogram(s) at step 802. A threshold amplitude value, $B_{amp}$, is then set at a value using linear interpolation wherein most of the Shannon energy transform signal 418 falls under at step 804. In particular, a straight line referred to as an interpolated straight-line is drawn connecting the minimum amplitude and maximum amplitude in the histogram. The difference between the amplitude-value on the interpolated straight-line (the line-value) and the amplitude-value on the histogram (the histogram-value) is then calculated. $B_{amp}$ corresponds to the greatest distance between the line-value and the histogram-value. FIG. 19 shows an example linear interpolation of histogram data, e.g. a representation of using linear interpolation to determine the $B_{amp}$ as also described in FIG. 8.

Figures 18A, 18B:
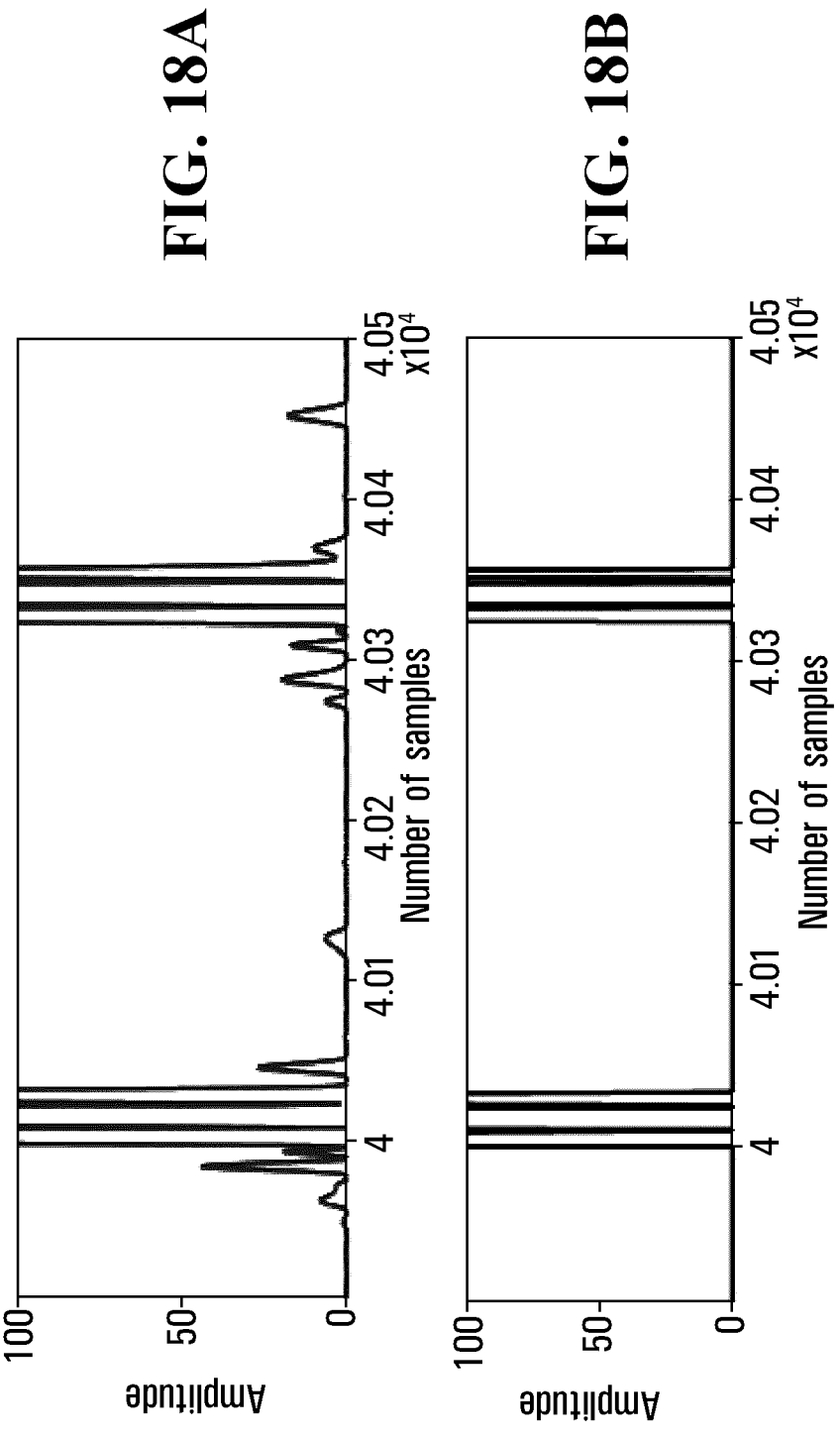
FIGS. 18A and 18B illustrate example graphs showing the processing of data that occurs in the histogram analysis stage of FIGS. 4 and 8 in accordance with an embodiment.

Referring back to FIG. 8, once the $B_{amp}$ is established, the Shannon energy transform signal 418 with amplitudes less than the $B_{amp}$ will have its amplitude transformed to zero 806. FIGS. 18A-18B show, as an example, the transformation of the amplitudes of the Shannon energy transform signal 418 to zero where it was less the $B_{amp}$. Specifically, FIG. 18A shows a Shannon energy transform signal 418 of FIG. 8 and FIG. 18B illustrates a potential QRS data 422 calculated in the histogram analysis step 420.

Figures 28A, 28B, 28C:
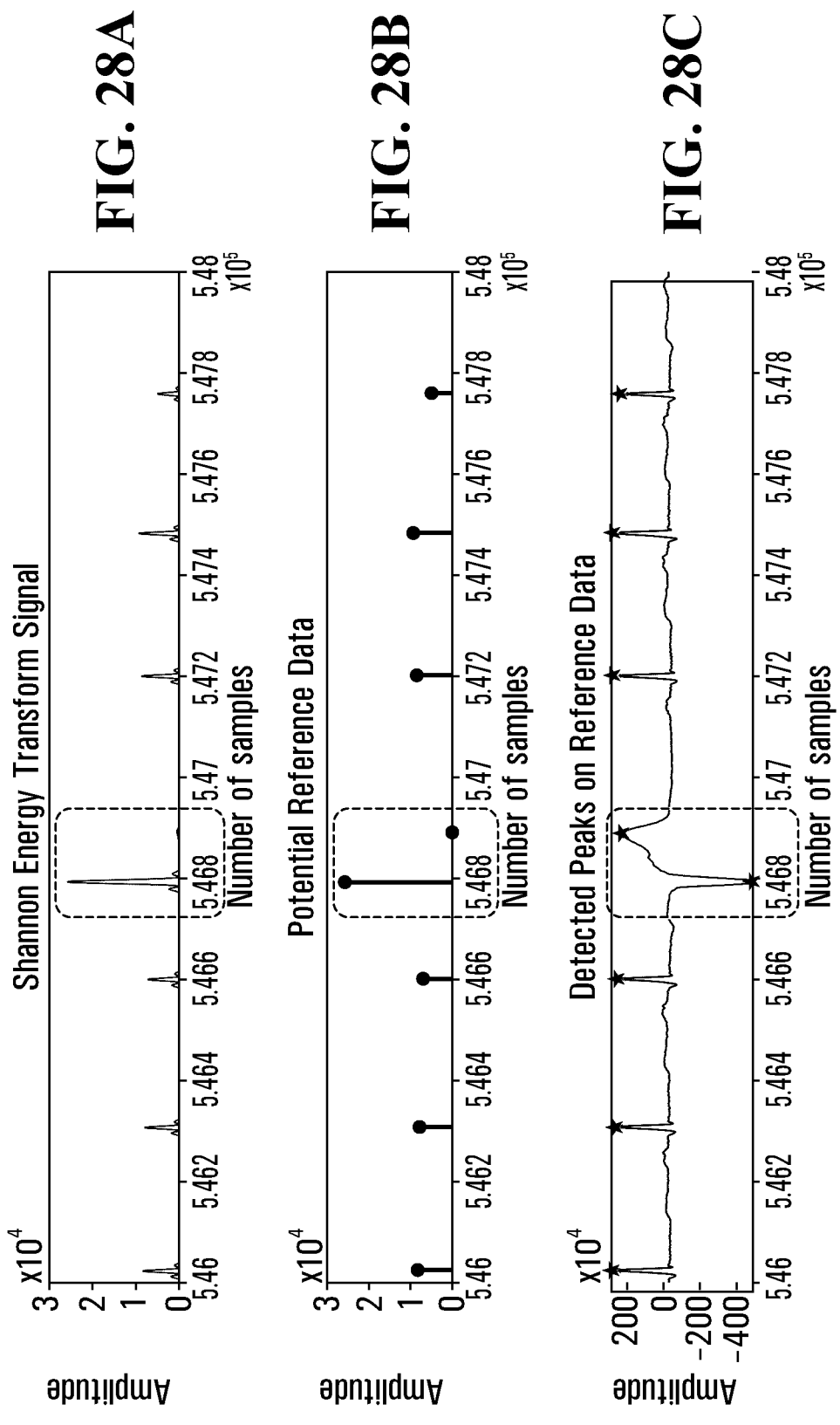
FIGS. 28A-28C illustrate example graphs showing a Shannon energy transform signal (FIG. 28A), detection of R-peaks (FIG. 28B) and mapping of R-peaks (FIG. 28C) from the Shannon energy transform signal onto the reference signal in accordance with an embodiment.

Since QRS-complexes are periodic, the histogram analysis 420 continues by segmenting the zero-transformed Shannon energy transform signal 418 into non-overlapping and fixed-sized windows of time 808. Ideally, the blocks of time should correspond to the maximum duration of a QRS-complex, which may, for example, be 150 milliseconds. Within each block, the maximum amplitude is determined at step 810 and only that particular datum is kept for subsequent processing; all other data are eliminated from further processing 812. The net result, the potential R data 422, is a single datum within each defined block of time representing the maximum amplitude within that particular window. The potential R-peaks data 422 are also representative of plausible R-peaks. FIG. 28A-C shows, as an example, the potential R-peaks data 422 mapped onto the reference signal 406. Specifically FIG. 28A illustrate a Shannon energy transform signal; FIG. 28B illustrates detecting potential R-peaks data (e.g. 422) and FIG. 28C illustrates detected peaks on the reference signal 406.

FIGS. 29A-G illustrate example graphs showing the series of transformations of the input ECG signal for the detection of peaks in the original input ECG signal in accordance with an embodiment as performed by the system of FIG. 1. Specifically, FIG. 29A illustrates an original ECG signal (e.g. as provided as input to the first difference 408 step); FIG. 29B illustrates a first difference modified signal of the signal in FIG. 29A (e.g. as provided as output from the first difference 408 step); FIG. 29C illustrates a Hilbert transform performed signal on FIG. 29B (e.g. as provided by Hilbert transform 412 step); FIG. 29D illustrates a histogram analysis output signal (e.g. as provided by histogram analysis 420 step); FIG. 29E illustrates another view of histogram analysis performed on FIG. 29C signal; FIG. 29F illustrates a modified Hilbert transform data signal illustrating the potential R-peaks data 422; and FIG. 29G illustrates all detected R-peaks of FIG. 29F mapped onto the original ECG signal.

Referring back to FIG. 4, in order to identify the corresponding Q and S-peaks within a particular QRS-complex, the potential R-peaks data 422 are mapped 424 onto the reference signal 406. The mapped onto reference signal can then be pruned 426 to detect the Q and S-peaks.

FIG. 9 shows a flowchart of pruning the non QRS-complexes at step 426 of FIG. 4. At step 902, the potential QRS data 422 identifies potential R-peaks. Mapped onto the reference signal 406, QRS-complexes 906 are first identified by using the potential R-peaks data 422 as reference points. At this stage of the process, potential R-peaks data are considered R-peaks of the QRS-complexes. By analyzing the minimum or maximum amplitudes on the mapped reference signal 406 within a fixed time interval from a particular R-peak, Q and S-peaks corresponding to the R-peak may then be identified at step 902. In particular, if the polarity of the R-peak is found to be positive, then the index of the minimum amplitude within a time boundary $t_R$ and $t_R - t_n$ is considered as the Q-peak. For that particular R-peak, the corresponding S-peak would be the minimum amplitude within the time boundary $t_R$ and $t_R + t_n$. Here, $t_R$ is the time corresponding to the R-peak.

If the polarity of the R-peak that has been mapped against the reference signal 406 is negative, then the index of the maximum amplitude identified within the $t_R - t_n$ and the $t_R + t_n$ time intervals for the corresponding Q and S-peaks, respectively.

According to one embodiment, the maximum duration of a QRS-complex is assumed to be 150 milliseconds. In this case, n would be equal to 75 milliseconds such that the Q-peak would be identified in the $t_R - 75$ milliseconds time interval and the S-peak would be identified in the $t_R + 75$ milliseconds time interval.

Once each QRS-complex 906 is identified, non-QRS-complexes are pruned. This process involves establishing a minimum time interval, $t_{SQ}$, between the S-peak of one QRS-complex and the Q-peak of the subsequent QRS-complex at step 904. The $t_{SQ}$ may be established based on factors such as the maximum heart rate. For example, if the maximum hear heart is assumed to be 240 beats/minute, then this would suggest that no two consecutive QRS-complexes could be closer than 250 milliseconds. Accordingly, in one embodiment, the $t_{SQ}$ may be set at 250 milliseconds.

Figures 20A, 20B:
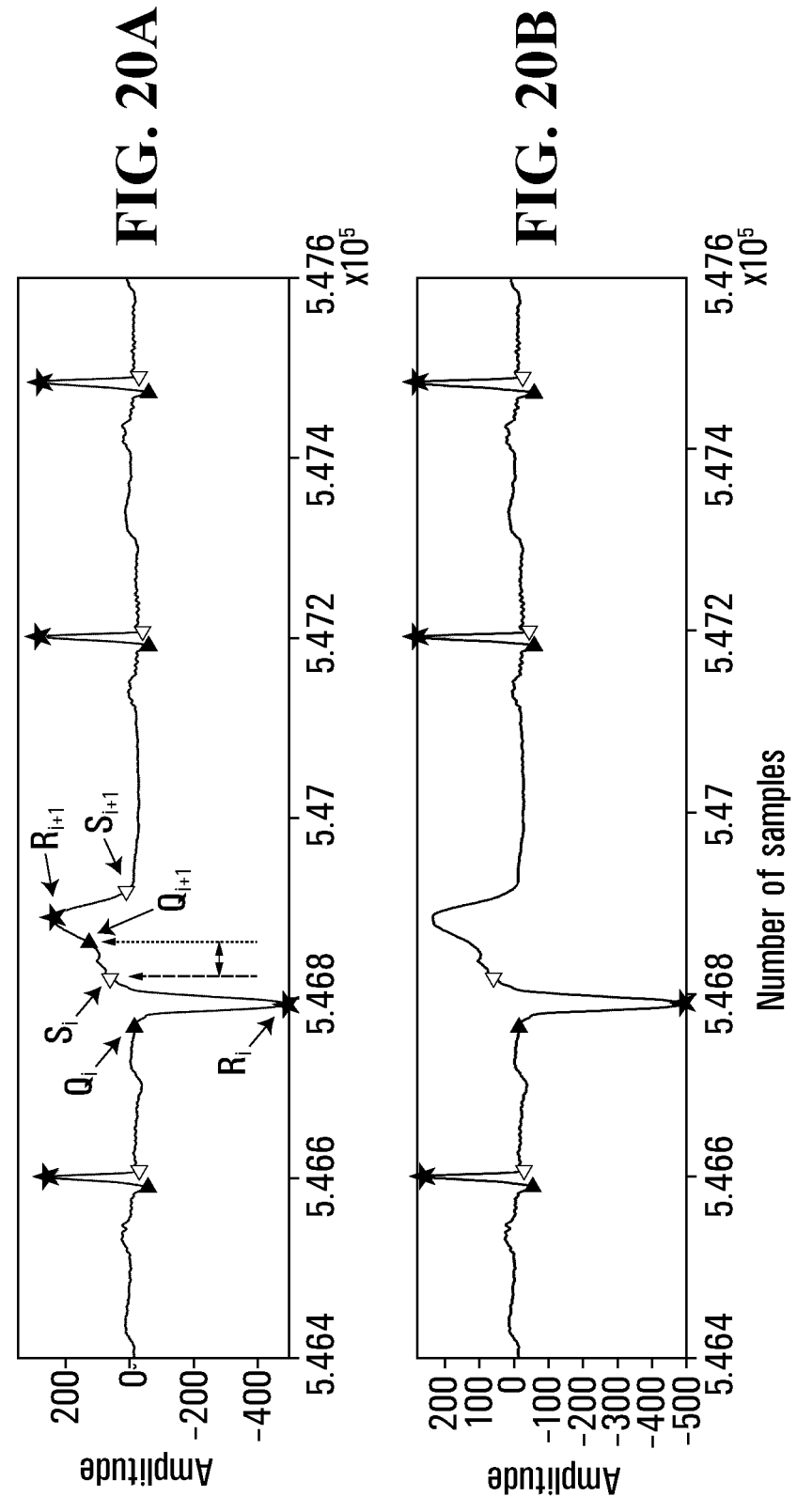
FIGS. 20A and 20B illustrate example graphs of the identification of QRS-complexes through pruning in the non-QRS-complex stage in FIGS. 4 and 9 in accordance with an embodiment.

QRS-complexes 906 shown in FIG. 9 are pruned for non-QRS-complexes by comparing the time interval between the S-peak in a QRS-complex, denoted as $S_i$, and the Q-peak in the subsequent QRS-complex, denoted as $Q_{i+1}$. If $Q_{i+1}-S_i$ is less than the $t_{SQ}$, then the QRS-complex that has the smaller R value is pruned or deleted at step 906. Once non-QRS-complexes are pruned at step 908, what remains, the preliminary ECG/QRS data 306, is considered the QRS-complexes of the ECG signal. FIG. 20A illustrates a potential QRS complex (e.g. complex 906 of FIG. 9) and FIG. 20B shows an example pruning of a non-QRS-complex, specifically preliminary ECG data 306 created by pruning the non-QRS complexes 426 of FIG. 20A.

From the QRS detection module 204 shown in FIGS. 2 and 3, the preliminary ECG/QRS data 306 is further processed in the residual noise module 206 for the detection of residual noise at 308. Residual noise may include MA and SCB noises, and may be detected more frequently and/or is more pronounced in low-frequency and low amplitude regions of the ECG signal such as the ST-segments, T-waves, TP-segments, and P waves, than compared to that of the high frequency and high amplitude counterparts.

Figure 5:
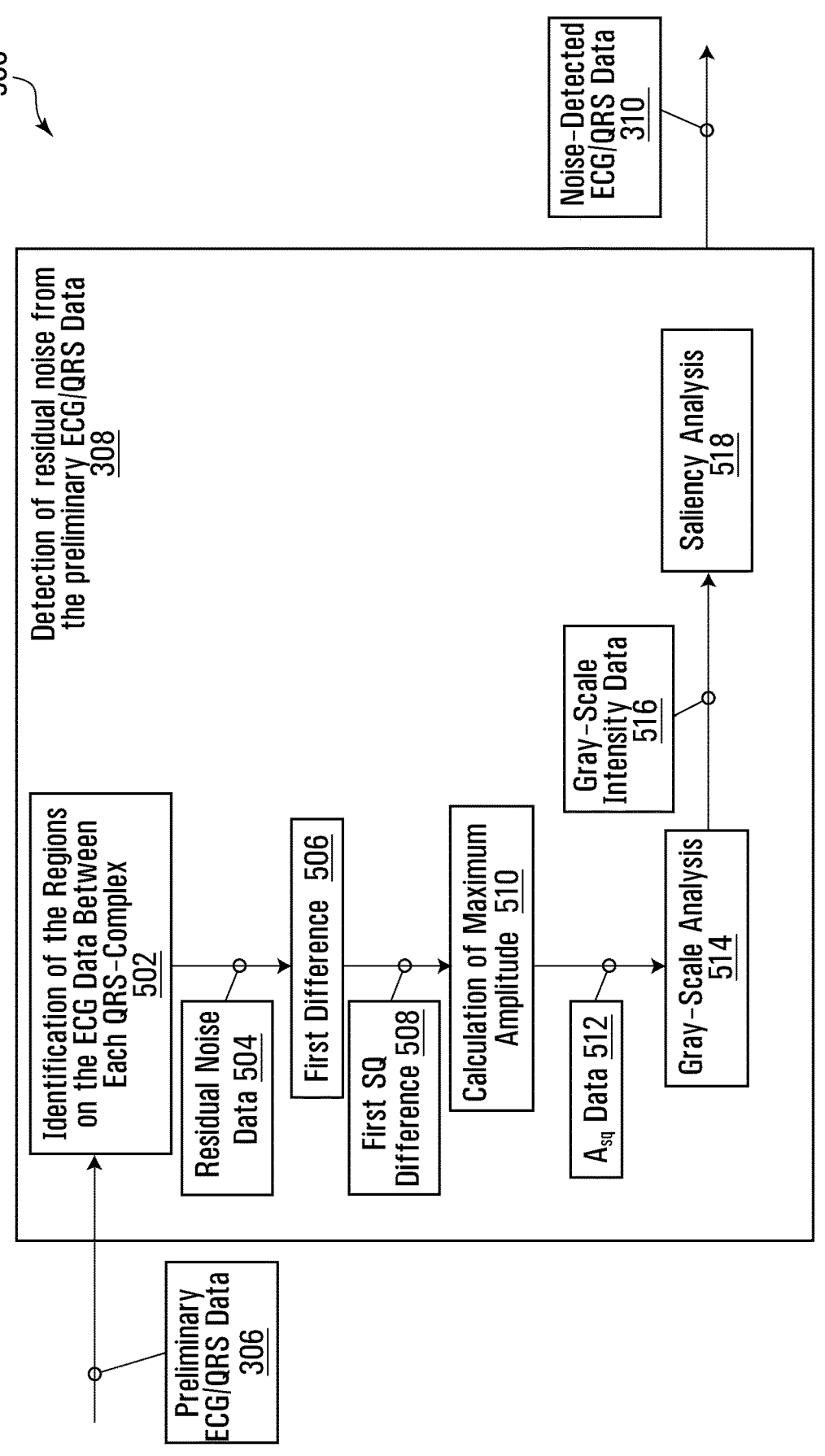
FIG. 5 is a flowchart showing example operations of the removal of residual noise from ECG signal as shown in FIG. 3, in accordance with an embodiment.

FIG. 5 is an example flowchart of operations 500 depicting the process of transforming regions of the preliminary ECG/QRS data 306 into an image as part of saliency analysis to detect MA and SCB noise, according to an embodiment. In this embodiment, the detection of MA and SCB at step 502 is focused on low-frequency and low amplitude regions of the ECG signal, namely, the region between $S_i$ and $Q_{i+1}$, denoted as $SQ_{reg}$, which corresponds to the residual noise data 504. Once the residual noise data 504 is calculated at step 502, the absolute-maximum amplitude of the first-difference of the residual noise data is calculated at step 506 using the following two formulas:

$$d_{SQ}^k = SQ_{reg_i}^k - SQ_{reg_{i-1}}^k \text{ and } A_{SQ}^k = \max \left| d_{SQ}^k \right|$$

Where, i varies from 2 to M, M is the length of every $SQ_{reg}$, k varies from 1 to L, L is the total number of QRS-complexes, and $A_{SQ}^k$ is the absolute-maximum amplitude of the first difference of the $k^{th}$ $SQ_{reg}$.

More specifically, the first difference 506 of each set of residual noise data 504, corresponds to the subtraction of two regions between $S_i$ and $Q_{i+1}$, e.g. consecutive regions, creating the first SQ difference 508. Then, the maximum amplitude $A_{sq}$ 512 of each set of first SQ difference 508 is identified in the calculation of maximum amplitude at step 510. An example of this operation can be seen in FIG. 21. An example of the operations of FIG. 5, are shown in FIG. 21A1, FIG. 21B1 and FIG. 21C1 by visual representation of the regions between $S_i$ and $Q_{i+1}$. FIG. 21A2, FIG. 21B2, and FIG. 21C2 shown are visual representation of the identification of $A_{sq}$ data 512 in the first difference data 508 between the QRS-complexes.

Figure 10:
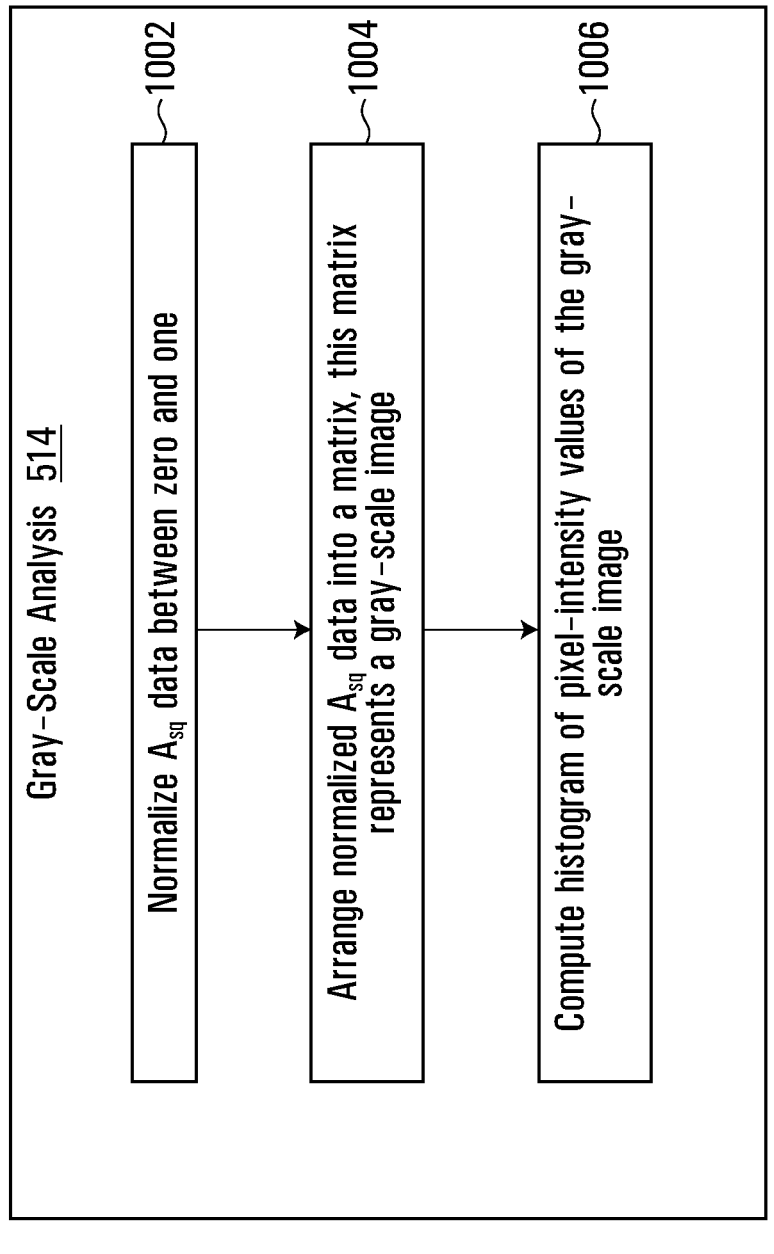
FIG. 10 is a flowchart showing example operation for the transformation of one-dimensional signal to two-dimensional gray-scale representation of a signal from the preliminary ECG/QRS data step, in accordance with an embodiment.

The $A_{SQ}$ data 512 is further processed in the gray-scale analysis at 514, which is shown in FIG. 10. In FIG. 10, the $A_{SQ}$ data 512 are first normalized between zero and one 1002 before they are arranged in the form of a gray-scale image 1004. The histogram of pixel-intensity values of the gray-scale image is then computed 1006 resulting the gray-scale intensity data 516.

FIG. 11 shows a flowchart of the saliency analysis operation 518, in accordance with an embodiment. The first step of the saliency analysis 518 is to detect peaks in the histogram at 1104. Upon comparing the intensities of two adjacent peaks, if the intensity-difference is found to be greater than or equal to a threshold, e.g. $Th_{int2}$, then the corresponding intensity value of the latter peak is considered as salient intensity, and those corresponding pixels are considered as salient pixels at 1106.

Figures 22A, 22B, 22C, 22D:
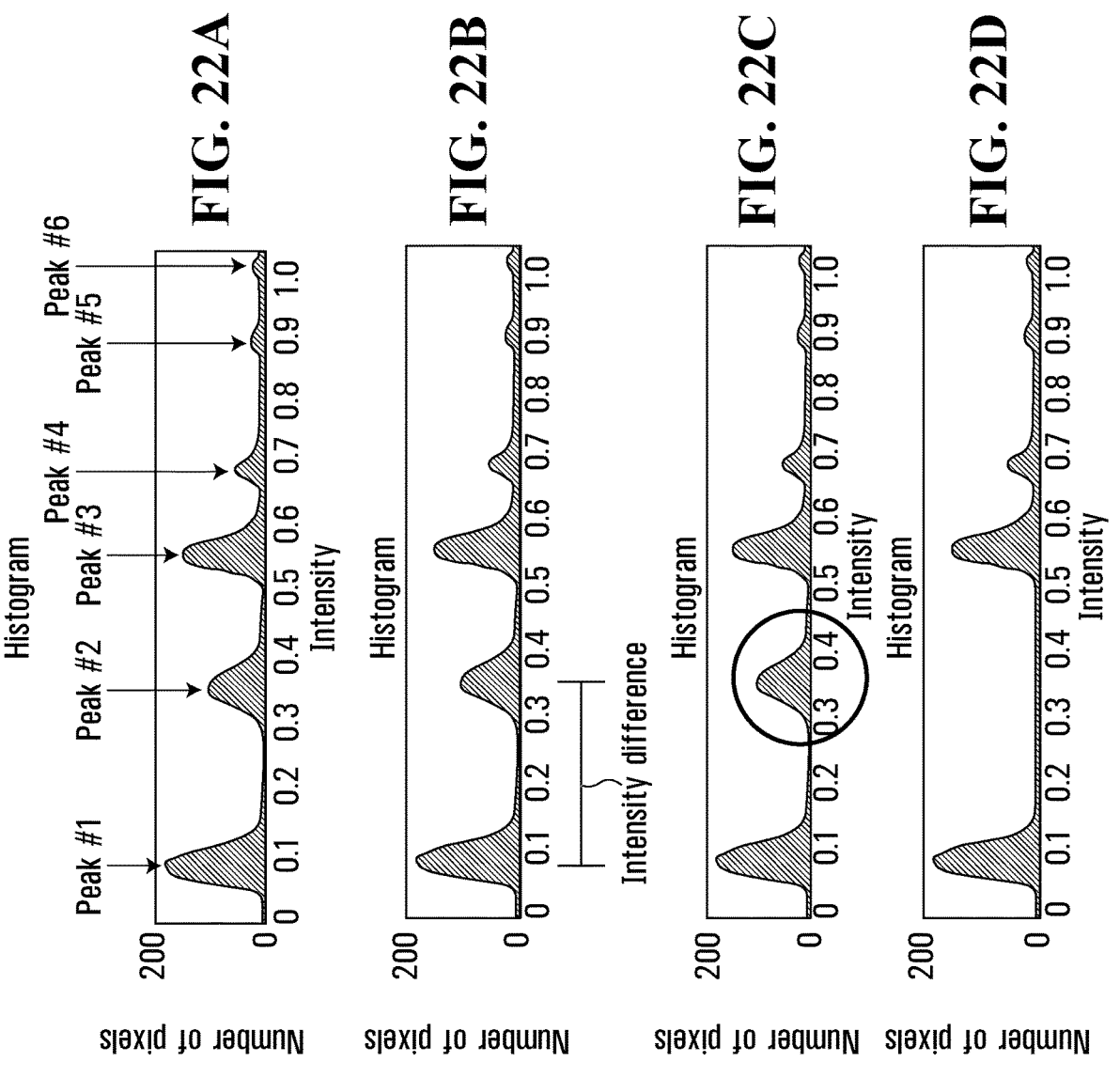
FIGS. 22A-D illustrate example graphs of the identification of MA and SCB noise using iterative histogram analysis as seen in FIGS. 5 and 11 in accordance with an embodiment.

Once the gray-scale image containing salient pixels is generated, the salient pixels are mapped onto the reference signal 406, and the corresponding data segments are marked as noise-contaminated at 1108. This process is executed iteratively excluding the histogram peak of the most recently detected salient intensity until there are no more peaks in the histogram with intensity difference greater than the $Th_{int2}$ 1110. FIGS. 22A-D shows example graphs of the saliency analysis process according to the methods of the present disclosure (e.g. saliency analysis 518 process shown in FIG. 11). Specifically, FIG. 22A illustrates an initial histogram featuring 6 peaks in intensity value of a histogram. FIG. 22B illustrates performing an intensity difference between peaks of FIG. 22A. FIG. 22C illustrates identifying a second peak, e.g. "peak 2" whose intensity difference with peak 1 is equal to or greater than the saliency threshold. FIG. 22D illustrates a graph with removal of "peak 2" prior to reiteration of histogram analysis (e.g. see also step 1110 of FIG. 11).

Figure 24:
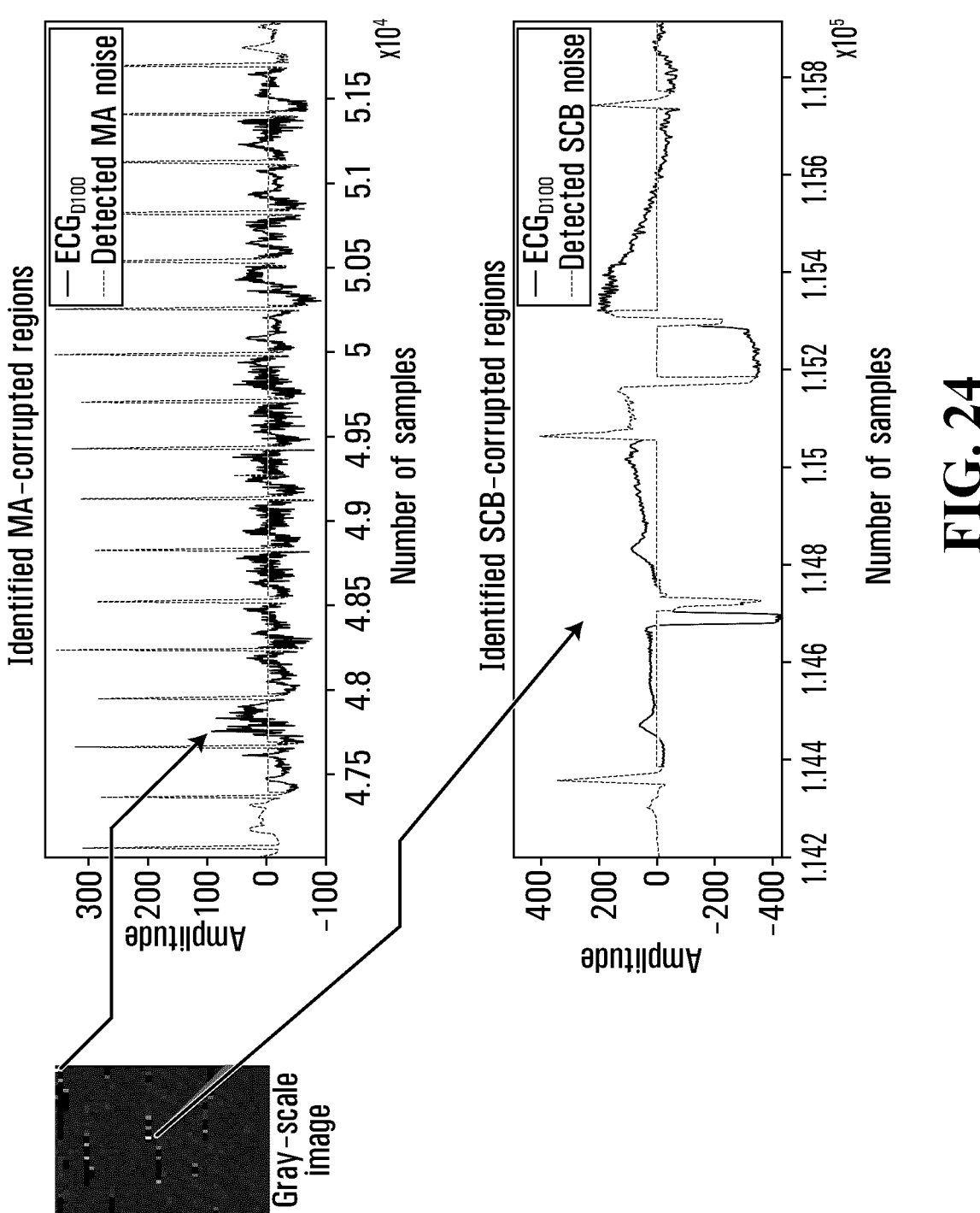
FIG. 24 illustrates example graphs showing the MA and SCB noise on a gray-scale image (shown on the left hand side) as also shown in FIG. 5 in accordance with an embodiment.

A visual representation showing corrupted regions in the gray-scale intensity data is shown in FIG. 24, according to one or more embodiments of the present disclosure. For example, FIG. 24 illustrates identified MA-corrupted regions 516 and detected SCB corrupted regions 516 as provided by the process 500 in FIG. 5.

$Th_{int1}$ and $Th_{int2}$ may be established and varied, in one embodiment, based on experimentation to determine when a pixel in a gray-scale image becomes visually salient. In another embodiment, $Th_{int1}$ and $Th_{int2}$ may be initially defined and subsequently dynamically adjusted via the system shown in FIG. 1 using one or more machine learning methods to predict subsequent thresholds based on prior used thresholds and/or prior similar applications and/or prior similar subjects where ECG data is used. In one embodiment, the $Th_{int1}$ and $Th_{int2}$ ranges from 0.1 to 0.3, and it is ideally 0.2.

Referring back to FIG. 3, the output of the signal resulting from the saliency analysis, the noise-detected ECG/QRS data 310, is processed for identification of abnormal QRS-complexes 312 in the identification module 208. Noise-detected ECG/QRS data corresponds to ECG signal with noise filtered. The abnormal QRS-complex identification technique is applied to the noise-detected ECG/QRS data.

Figure 6:
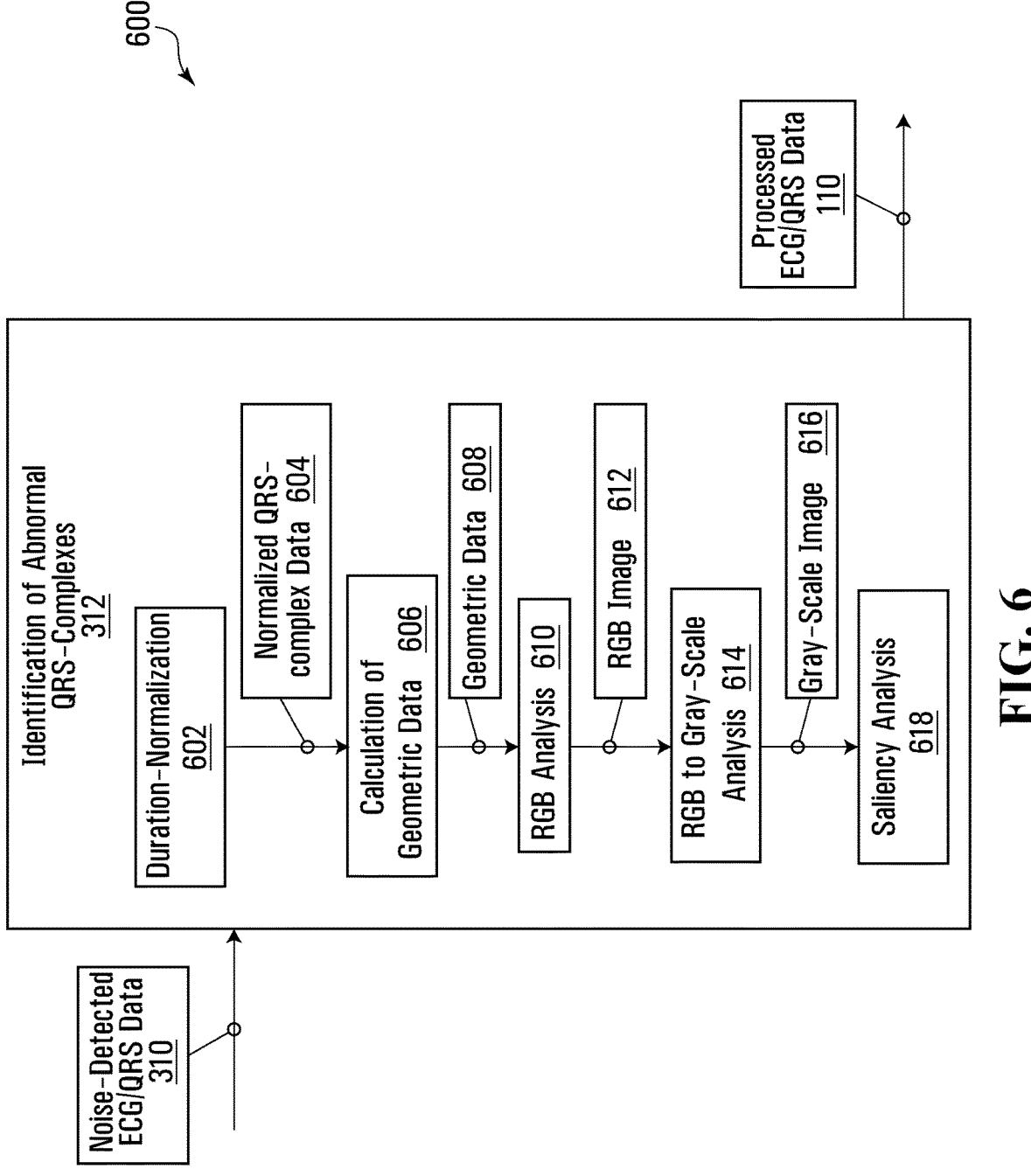
FIG. 6 is a flowchart showing example operations of the identification of abnormal QRS-complexes as shown in FIG. 3, in accordance with an embodiment.

FIG. 6 is a flowchart of the process operations 600 for identifying abnormal QRS-complexes 312 by representing QRS-complexes' geometric measures as an image corresponding to QRS-complexes as part of saliency analysis, according to an embodiment. First, the duration of every QRS-complex in the noise-detected ECG/QRS data 310 is normalized 602. This may be achieved by using the fast Fourier transform-based interpolation technique. The normalized QRS-complex data 604 is then used to calculate geometric data 608 using calculation of geometric data 606. In particular, three unique geometric features are extracted, namely, QRS-angle (QRS$^o$), QRS-area (QRS$^a$), and QRS-height (R$^h$).

Figures 23A, 23B:
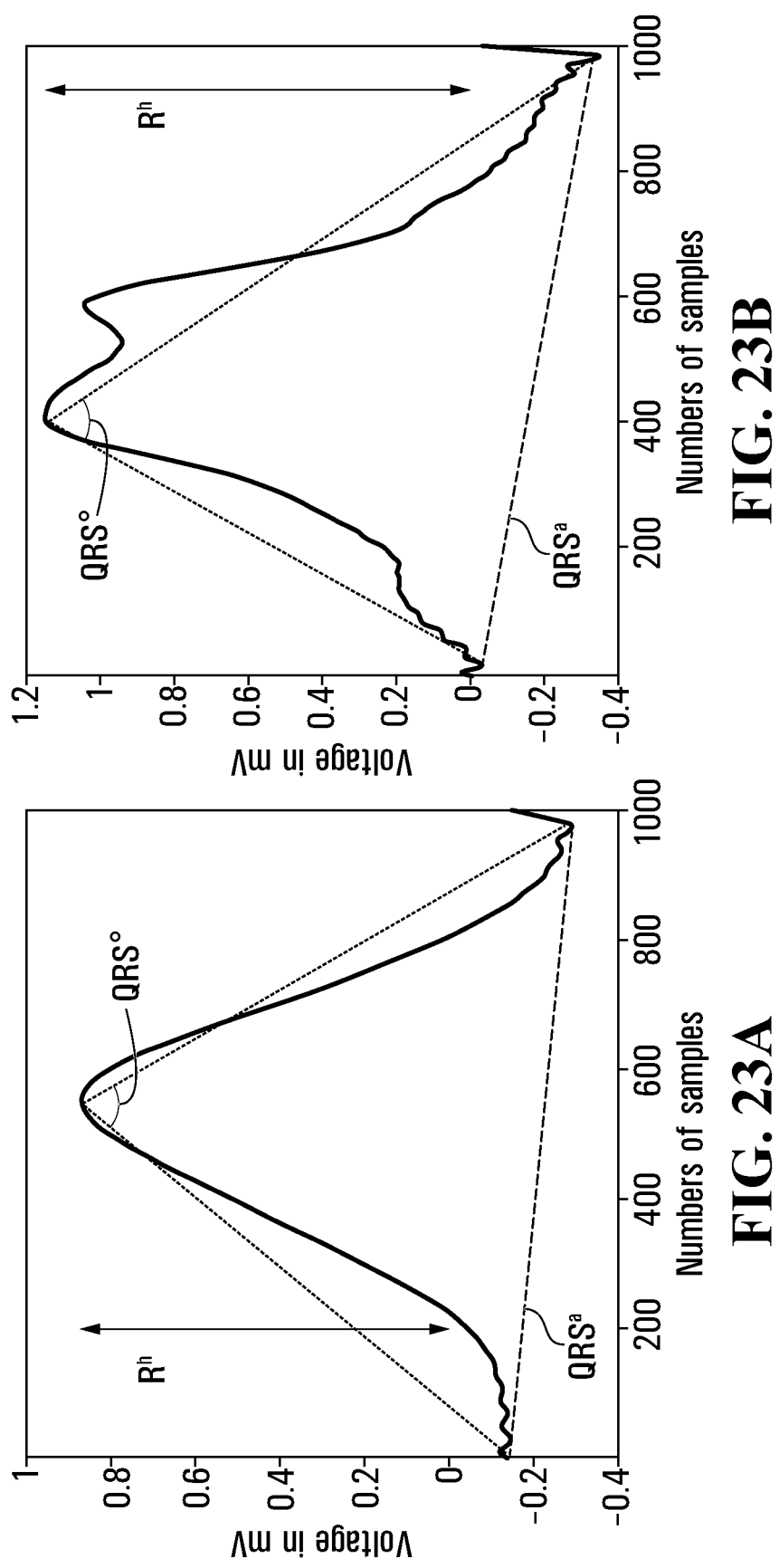

R$^h$ corresponds to the amplitude of the R-peak, which is identified as the highest amplitude within the normalized QRS-complex. QRS$^a$ can be calculated using the trapezoidal rule. QRS$^o$ of the normalized QRS-complex is the angle created between the Q, R, and S-peaks. It can be calculated through the following equation:

$$QRS^o = \cos^{-1}\left(\frac{\overrightarrow{QR} \cdot \overrightarrow{RS}}{\|\overrightarrow{QR}\| \cdot \|\overrightarrow{RS}\|}\right) \quad (2)$$

Where $\overrightarrow{QR}$ is the distance between the Q-peak and the R-peak in the triangle created by connecting the Q, R, and S-peaks. $\overrightarrow{RS}$ is the distance between the R-peak and S-peak. A visual representation of the angle, height, and area of a QRS-complex is shown in FIG. 23A-B.

Figure 30:
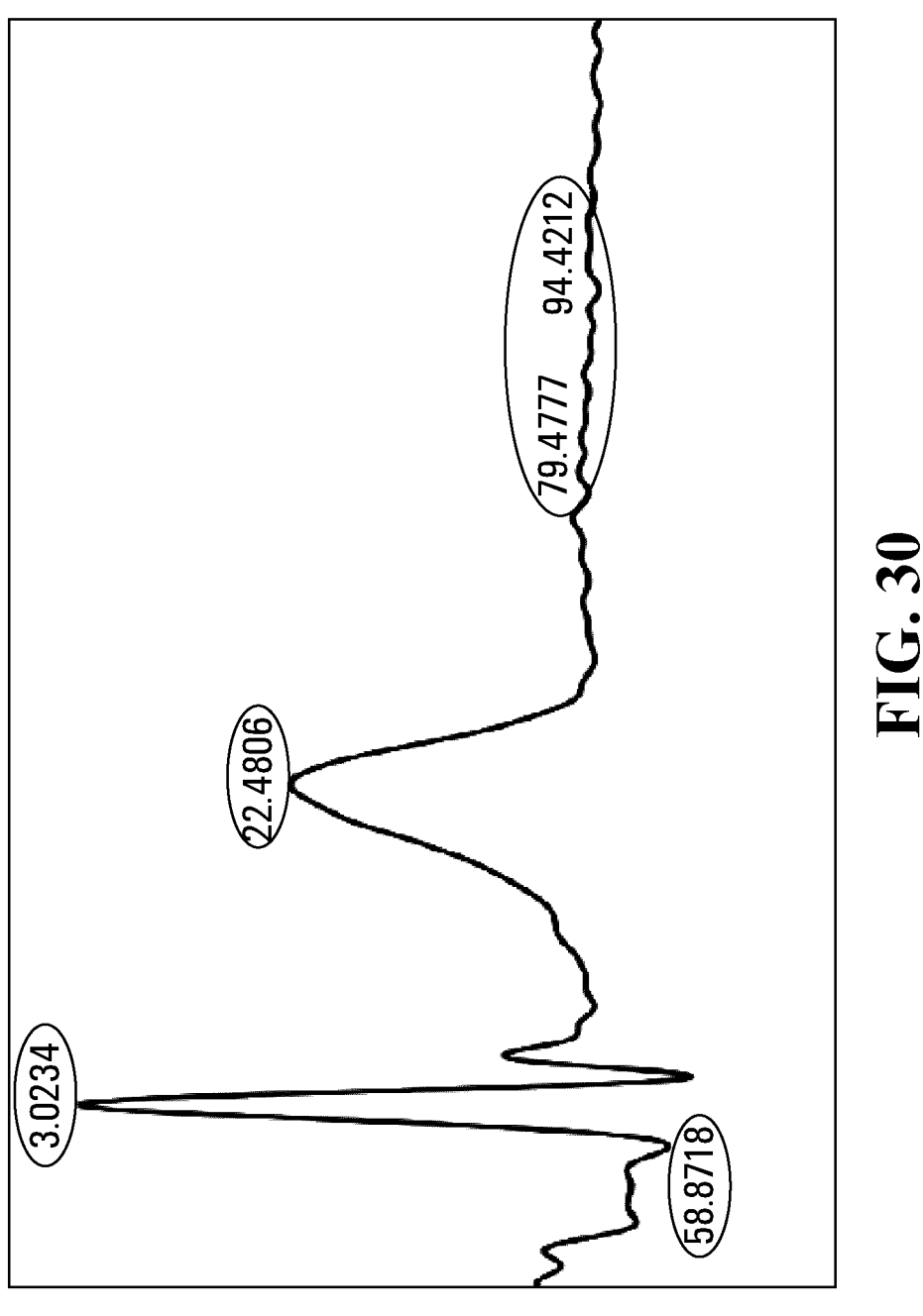
FIG. 30 illustrates an example graph showing calculated angles of various different detected peaks in accordance with an embodiment.

The QRS$^o$ is considered fairly consistent between QRS-complexes and, therefore, may function as an important indicator of abnormal QRS-complexes. Generally, the angle of an R-peak is much less than the angle of other peaks in QRS-complexes. FIG. 30 shows, as an example, a comparison of the calculated angles at different peak points.

Figure 12:
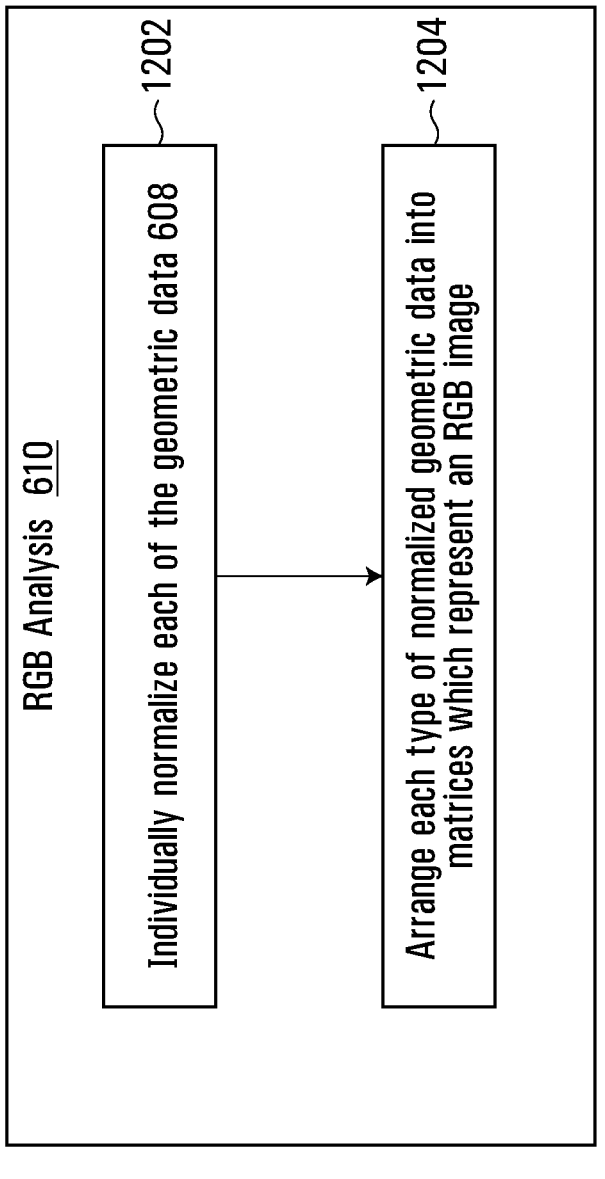
FIG. 12 is a flowchart showing example operation for transformation of one dimensional signal to two-dimensional RGB representation used to identify the abnormal QRS-complexes as shown in FIG. 6 in accordance with an embodiment.

The three-dimensional geometric data 608 (QRS$^a$, R$^h$, and QRS$^o$) is then converted into an RGB image 612 through RGB analysis 610. Each dimension of the geometric data corresponds to a plane in the RGB image. FIG. 12 is a flowchart of the process for RGB analysis 610, according to an embodiment. The value of each geometric data, QRS$^a$, R$^h$, and QRS$^o$, is first individually normalized against their corresponding maximum-normal values 1202. These maximum-normal values 1202 may be calculated by experimentation, and in one embodiment, may be 2 millivolts for R$^h$, 5$^o$ for QRS$^o$ and 1.5 for QRS$^a$.

Figure 25:
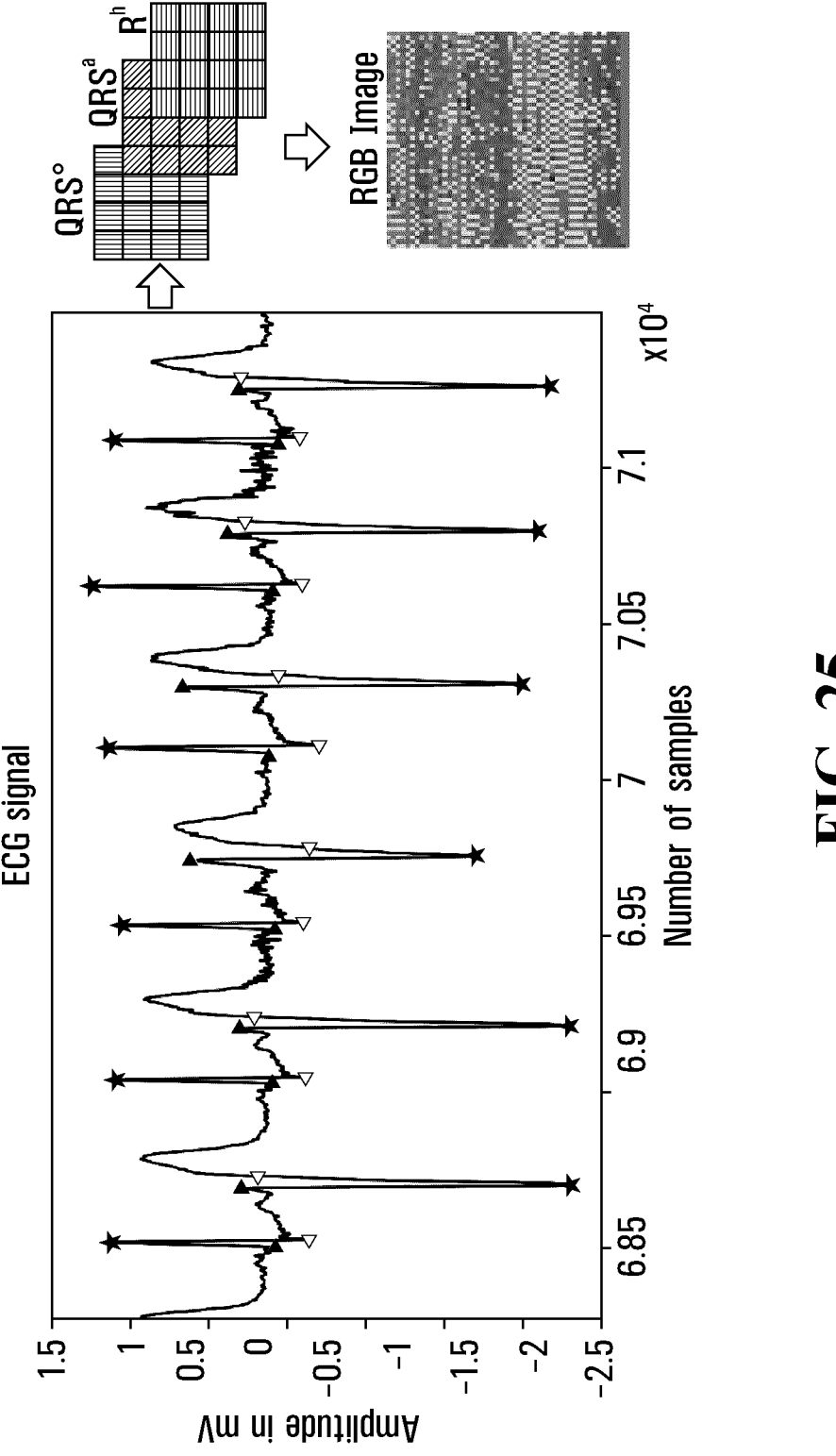
FIG. 25 illustrates example graphs representing QRS-complexes geometric calculation as an RGB image as seen in FIG. 6 in accordance with an embodiment. The left hand side

Each of the normalized geometric data are then arranged in the form of a matrix or tensor which are subsequently arranged to create an RGB image 1204. The arrangement of these three matrices represents an RGB image 612. Each pixel is represented by geometric date from the same QRS-complex. FIG. 25 is a visual representation of the RGB image where the red image corresponds to the normalized QRS$^o$ matrix, the green image corresponds to the normalized QRS$^a$ matrix, and the blue image, corresponds to the normalized R$^h$ matrix.

Figure 27:
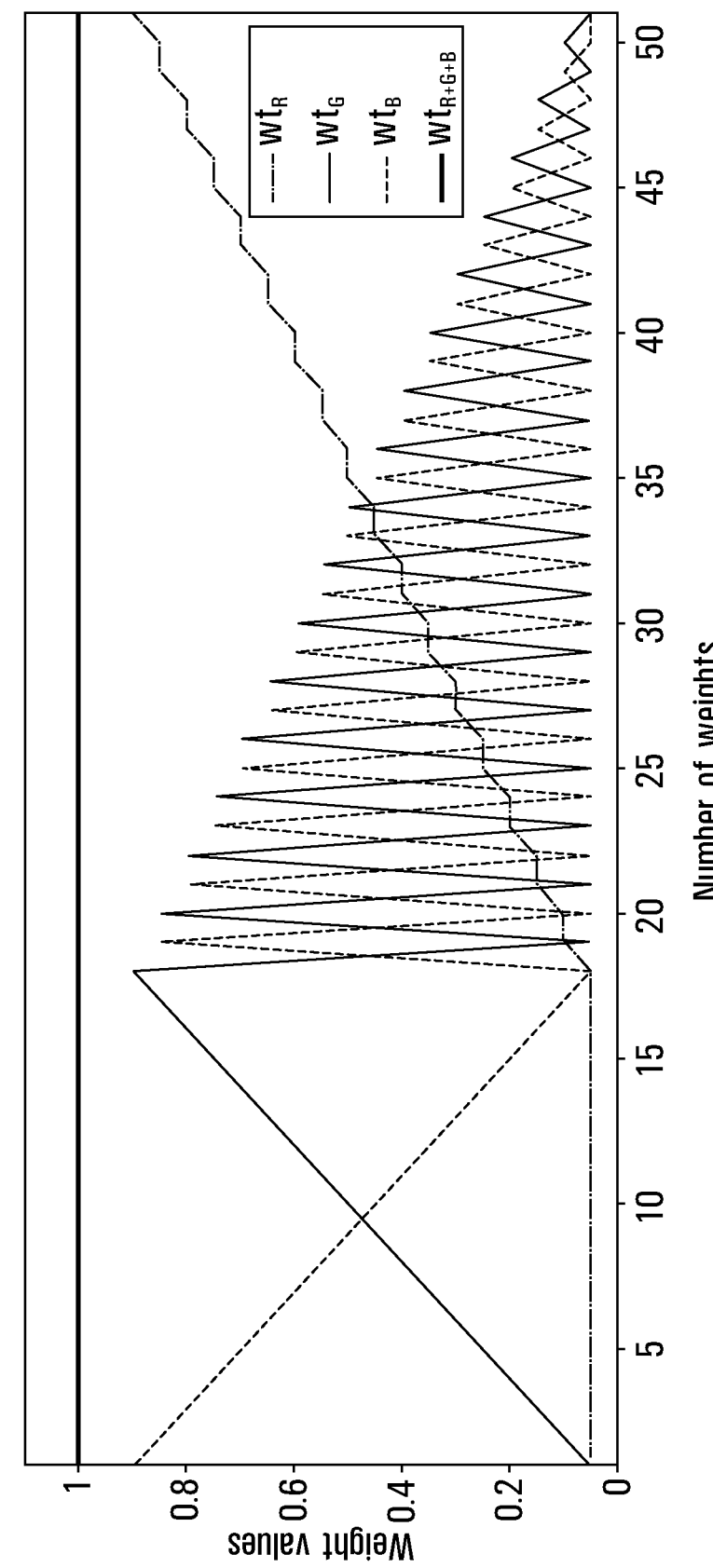
FIG. 27 illustrates an example graph showing the various combinations of weight values of R, G and B components assigned to the individual components of an RGB image in accordance with an embodiment.

Since abnormality may be detected in any of the three R, G, and B images, the RGB to gray-scale analysis 614 uses a range of different weight values rather than fixed weight values assigned to all the R, G, and B components. In one embodiment, the variation of different weight values is summarized and represented by the following equation and in FIG. 27:

$$G_{image}^i = (wt_R \times R) + (wt_G \times G) + (wt_B \times B) \quad (3)$$

Where $$G_{image}^i$$

is the i$^{th}$ gray-scale image, where i is 1, 2, 3, . . . 51, and wt$_R$, wt$_G$, and wt$_B$ are the weights of the R, G, and B images. Each weight varies from 0.05 to 0.9, and have a step-size of 0.05. Further, the sum of the weights (wt$_R$+wt$_G$+wt$_B$) must equal one.

In this particular example, this approach wherein a range of different weight values are assigned generates a set of 51 gray-scale images 616 for every unique combination of wt$_R$, wt$_G$, and wt$_B$ values.

Figure 13:
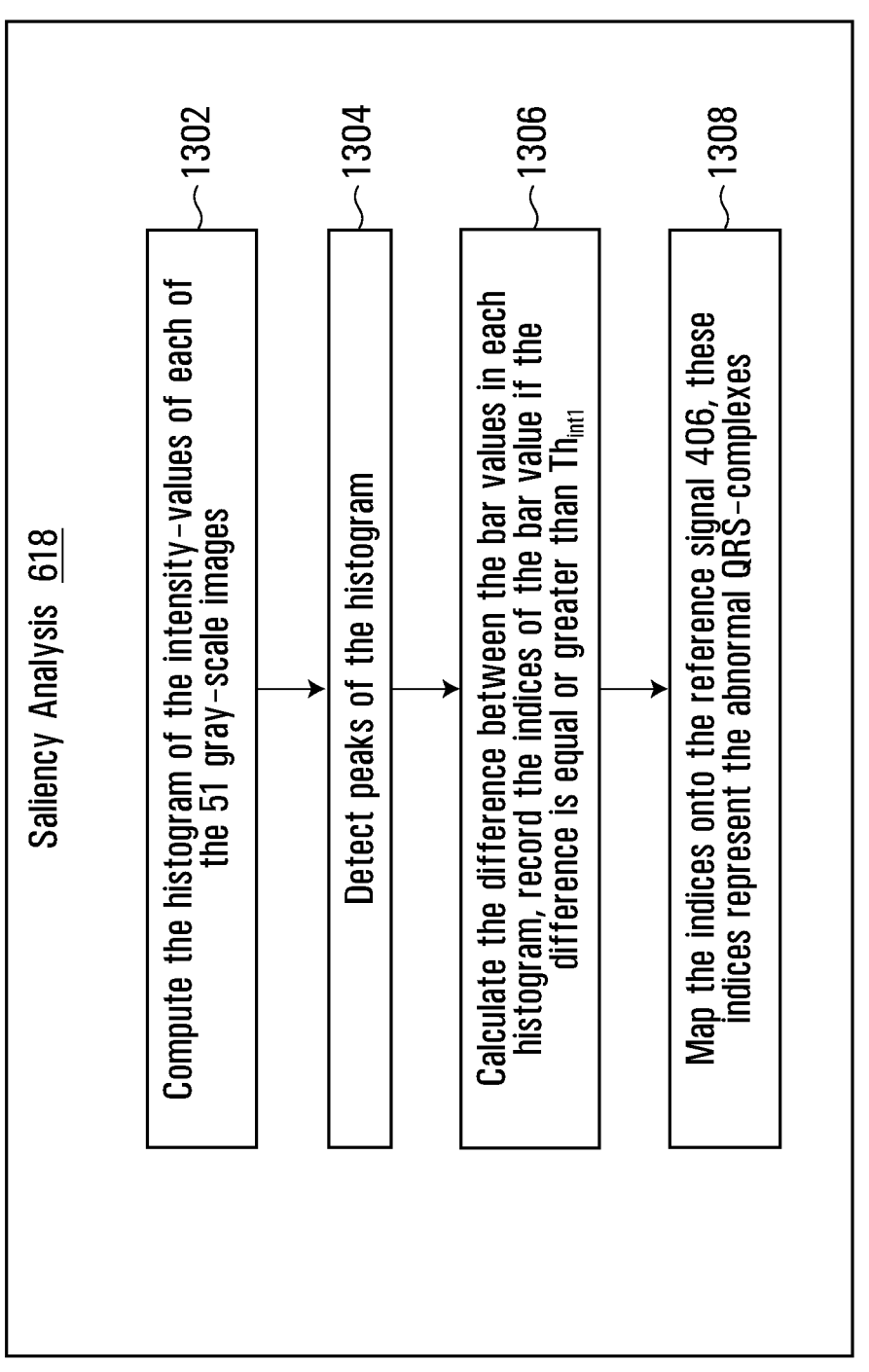
FIG. 13 is a flowchart showing example operation of the saliency analysis used to identify the abnormal QRS-complexes as shown in FIG. 6 in accordance with an embodiment.

In order to identify the salient pixels of each of the gray-scale images 616, the gray-scale images 616 are processed through saliency analysis 618. FIG. 13 is a flowchart of the processes in the saliency analysis 618. First, a histogram of the pixel-intensity values of the i$^{th}$ gray-scale images is calculated 1302. The peak values of the histograms are subsequently detected 1304 and compared. If any peak on the histogram data is found to have an intensity difference greater than or equal to Th$_{int1}$, as compared to its previous S-peak, then that corresponding intensity value is considered as a salient intensity, and those corresponding pixels are considered as salient pixels 1306.

The salient pixels are mapped onto the reference signal 406, and the corresponding QRS-complexes are considered abnormal 1308. This technique of identifying abnormal QRS-complexes is applied to all gray-scale images.

Figure 26:
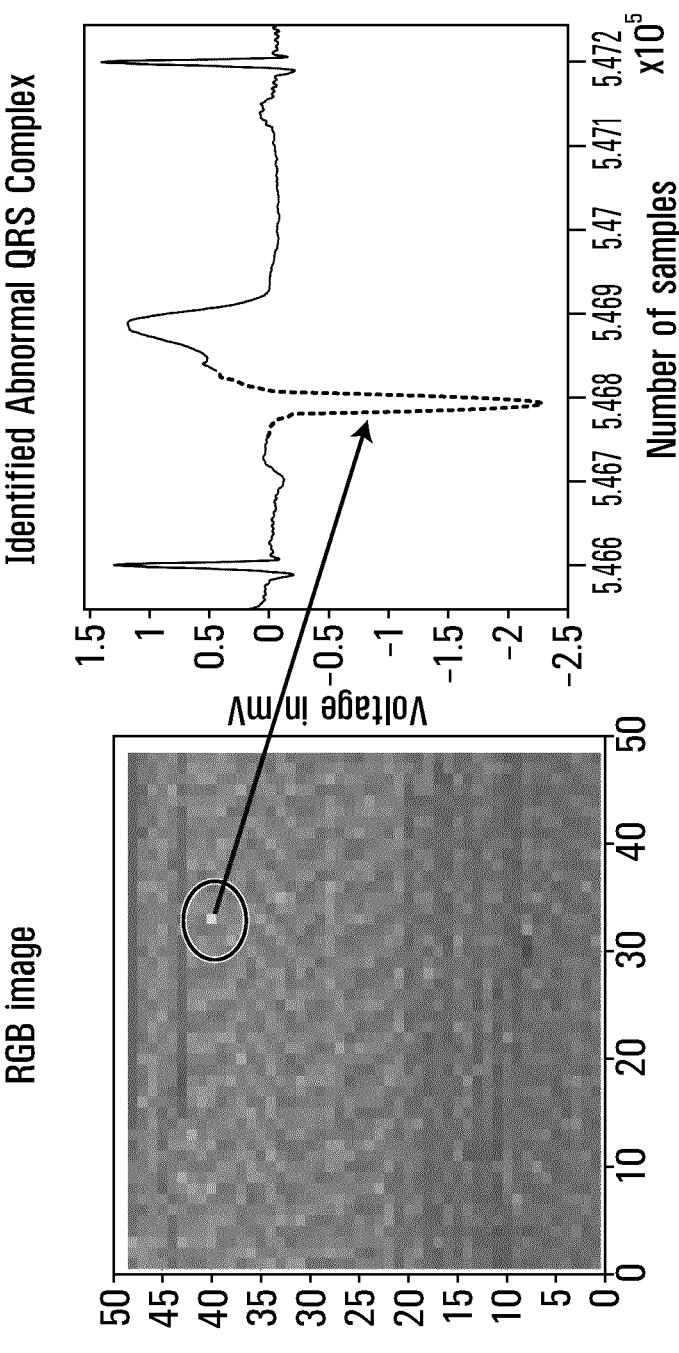
FIG. 26 illustrates example graphs showing the identification of an abnormal QRS-complex in an RGB image as seen in FIG. 6 in accordance with an embodiment.
Figure 31:
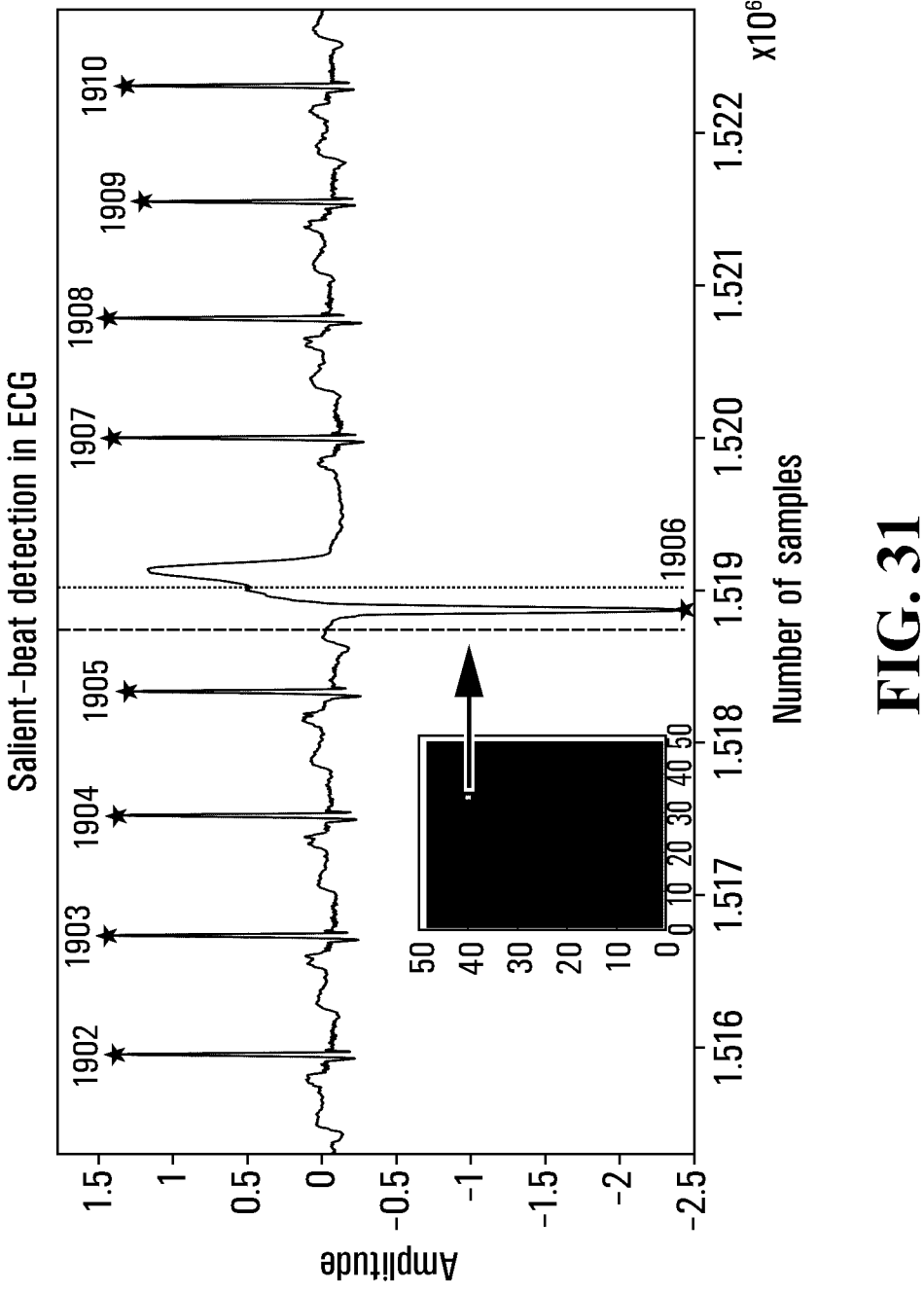
FIG. 31 illustrates an example graph showing detection of abnormal QRS-complex through the mapping of a salient pixel onto the reference signal in accordance with an embodiment.
Figure 32:
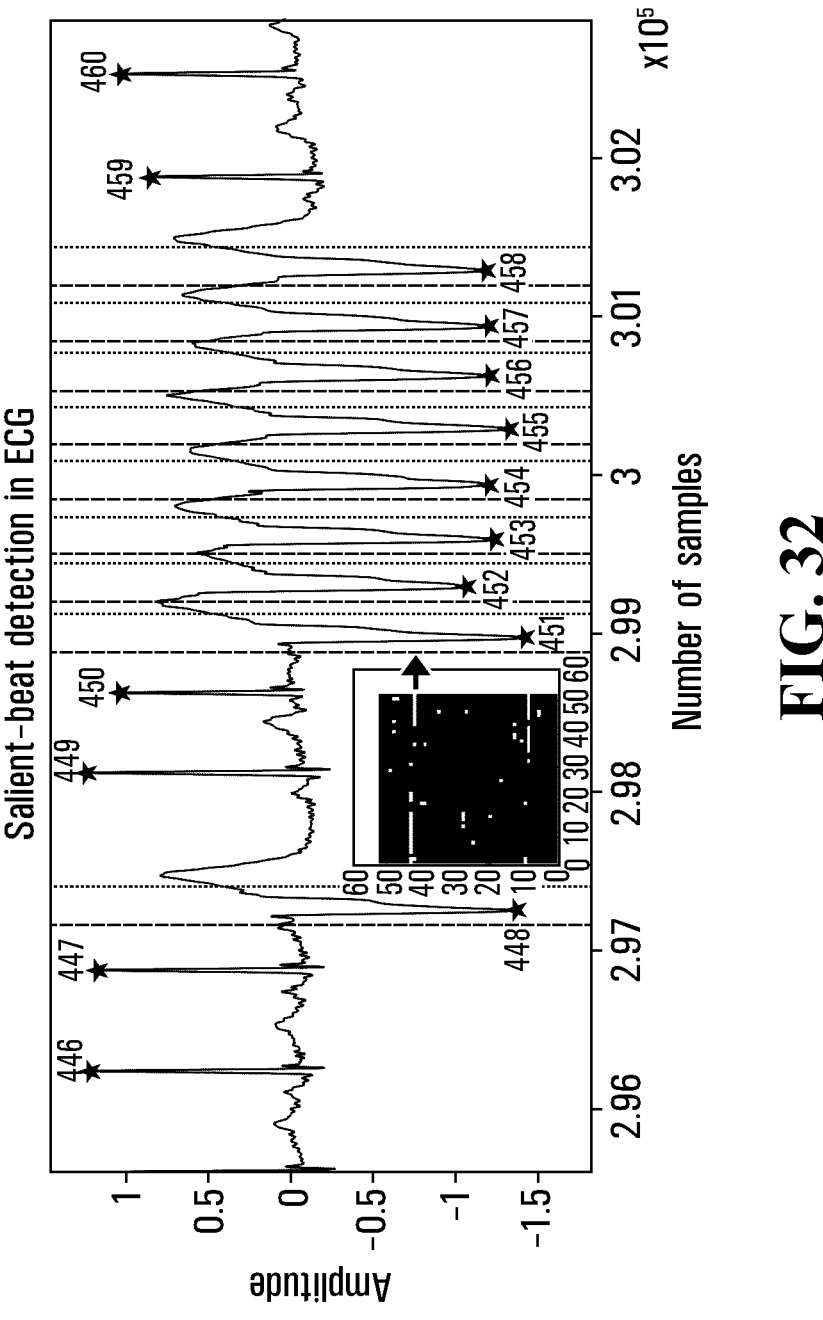
FIG. 32 illustrates an example graph showing detection of abnormal QRS-complexes through the mapping of salient pixels onto the reference signal in accordance with an embodiment.

FIGS. 26, 31, and 32 show a visual representation of the RGB image with a corrupted QRS-complex. Namely, the left hand side image in FIG. 26 illustrates an RGB image 612 and the right hand side image in FIG. 26 illustrates an identified abnormal QRS complex. FIG. 31 illustrates a graph of using saliency analysis to identify abnormal QRS complex and similarly FIG. 32 illustrates another example of using saliency analysis to identify an abnormal QRS complex in a different signal. The RGB image of FIG. 26 may be provided from an ECG signal shown in the left hand side image in FIG. 25 by performing an RGB analysis (e.g. shown as RGB analysis 610 in FIG. 6) to provide the RGB image of the normalized feature values 612 in the right hand side image in FIG. 25.

After saliency analysis, the processed data become the processed ECG/QRS data 110 and represents both the noise-filtered ECG signal, as well as the indices of both the normal and abnormal QRS-complexes. This processed ECG/QRS data 110 (e.g. as shown in FIG. 1) is then sent to the client monitoring device 112 for further analysis via diagnostic examination 314 (See FIG. 3).

FIG. 36 shows a flowchart of the process for identifying abnormal QRS-complexes 312 by representing QRS-complexes' geometric measures as an image corresponding to QRS-complexes as part of saliency analysis, according to an embodiment. The input at 3602 corresponds to the preliminary ECG/QRS data 306, which contains detected QRS-complexes, that may be sent by the processor 218 to the memory 220. The first step is to calculate geometric data using calculation of geometric data 606. This step includes calculating QRS-height, QRS-area, and QRS-angle of every QRS-complex 3604.

The QRS-height corresponds to the amplitude of the R-peak, which is identified as the highest amplitude within the QRS-complex. The QRS-area can be calculated using the trapezoidal rule. The QRS-angle is the angle created between the Q, R, and S-peaks, can be calculated as in equation (2), above.

Each of the three geometric data is normalized to a range between 0 and 1 3606. Each of the three normalized geometric data is then arranged into a two-dimensional matrix, which represents an image 3608. The constructed three two-dimensional images represent an RGB image 3610. This RGB image is transformed to a plurality of gray-scale images by applying equation 3, above, by assigning different weight values to $wt_R$, $wt_G$, and $wt_B$ using RGB to gray-scale analysis 614. The plurality of gray-scale images depends on the number of combinations of $wt_R$, $wt_G$, and $wt_B$. The weight values of $wt_R$, $wt_G$, and $wt_B$ are of any number between 0 and 1 with the condition that the sum of the three weight values must equal to one 3612.

Salient pixels in the plurality of gray-scale images correspond to abnormal QRS-complexes 3614. In order to identify the salient pixels of each of the plurality of gray-scale images, the gray-scale images are processed through saliency analysis 618. The histogram of each gray-scale image is calculated and every peak is compared to previous peaks. If any peak of the histogram has an intensity difference greater than or equal to $Th_{int1}$, then that intensity is recorded as a salient intensity. Correspondingly, the pixels of the gray-scale images with such intensity are salient pixels, which represent abnormal QRS-complexes 3616.

The salient pixels are mapped onto the reference signal 406 to locate the abnormal QRS-complexes. Different values of the saliency threshold, $Th_{int1}$, identifies different types of QRS-complexes.

Figure 33:
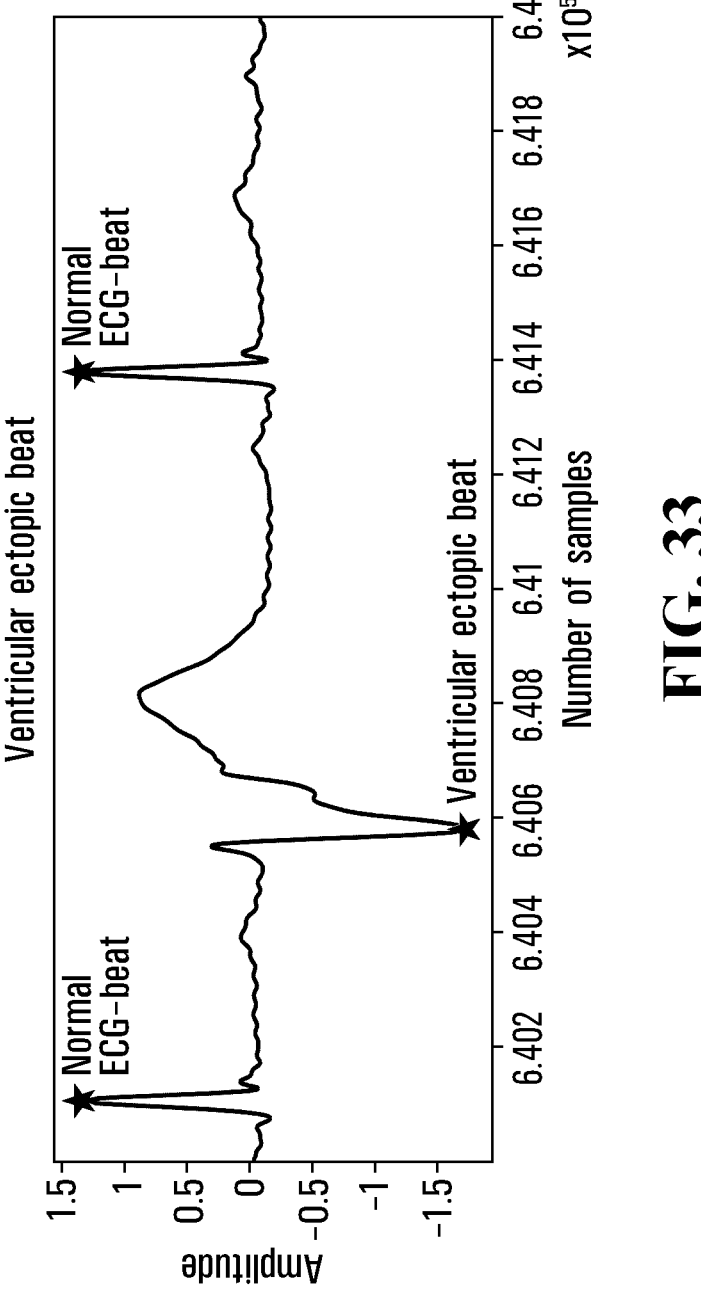
FIG. 33 illustrates an example output graph showing the color coding and identification of an abnormally detected heartbeat (e.g. color coded QRS complexes), namely ventricular ectopic beat as provided by the computing system of FIG. 1 in accordance with an embodiment.
Figure 34:
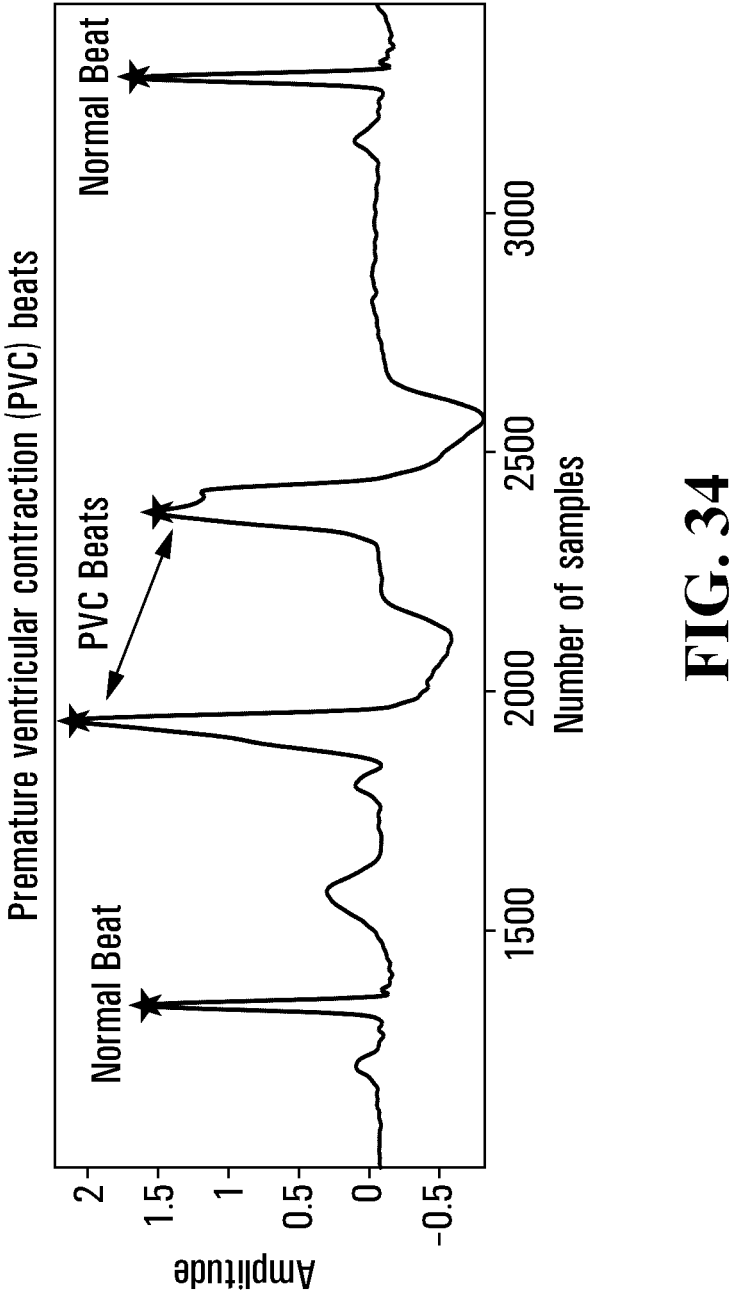
FIG. 34 illustrates as example output graph showing the color coding and identification of an abnormally detected heartbeat, namely premature ventricular contraction (PVC) beat as provided by the computing system of FIG. 1 in accordance with an embodiment.

In another embodiment, the processed ECG/QRS data 110 may include added features or annotations which enable the patient to better understand his/her ECG signal and heart condition without the assistance of a medical professional. For example, different QRS characteristics may be indicated by different colors such that an abnormal ECG signal can be easily identified by a patient by using a reference guide of what each color represents. FIGS. 33 and 34 are two example graphs of abnormal ECG signals where the abnormally identified beats (ventricular ectopic beat in FIG. 33 or premature ventricular contraction beats in FIG. 34) may be color coded differently than beats that are identified as normal. Other abnormalities that may be identified by this system include bundle branch block, myocardial infraction, and ischemia.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit.

Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium. By way of example, and not limitation, such computer-readable storage media can comprise RAM, ROM, EEPROM, optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using wired or wireless technologies, such are included in the definition of medium. It should be understood, however, that computer-readable storage media and data storage media do not include connections, carrier waves, signals, or other transient media, but are instead directed to non-transient, tangible storage media.

Instructions may be executed by one or more processors, such as one or more general purpose microprocessors, application specific integrated circuits (ASICs), field programmable logic arrays (FPGAs), digital signal processors (DSPs), or other similar integrated or discrete logic circuitry. The term "processor," as used herein may refer to any of the foregoing examples or any other suitable structure to implement the described techniques. In addition, in some aspects, the functionality described may be provided within dedicated software modules and/or hardware. Also, the techniques could be fully implemented in one or more circuits or logic elements. The techniques of this disclosure may be implemented in a wide variety of devices or apparatuses, an integrated circuit (IC) or a set of ICs (e.g., a chip set).

One or more currently preferred embodiments have been described by way of example. It will be apparent to persons skilled in the art that a number of variations and modifications can be made without departing from the scope of the invention as defined in the claims.

What is claimed is:

1. A computer-implemented method for identifying abnormal QRS-complexes in an ECG signal comprising:

receiving an ECG signal with detected QRS-complexes, the ECG signal captured by a sensor; and at an identification module implemented using at least one processor:

calculating a plurality of geometric measures of the QRS-complexes comprising: QRS-angle, QRS-area, and QRS-height;

normalizing the geometric measures;

constructing an RGB image with three two-dimensional matrices, representing the R, G, and B planes of the RGB image, each matrix corresponds to one of the calculated plurality of geometric measures, the geometric measures belonging to one QRS-complex have the same matrix index across the three two-dimensional matrices;

generating a plurality of gray-scale images based on the RGB image;

computing histograms of each of the plurality of gray-scale images; iteratively comparing every histogram peak to its previous one;

generating a plurality of salient gray-scale images by selecting salient pixels from pixels in the plurality of gray-scale images using saliency detection to select pixel intensities corresponding to histogram peaks with a difference value of equal or greater than a predefined threshold, a saliency threshold ($Th_{int1}$);

mapping salient pixel indices of the salient gray-scale images onto the ECG signal;

classifying respective indices on the ECG signal as abnormal QRS complexes; and outputting the abnormal QRS complexes.

2. The method of claim 1, wherein the QRS-complexes on the ECG signal are detected by:

receiving the ECG signal containing QRS-complexes from the sensor;

preprocessing the ECG signal to de-noise the ECG signal generating a preprocessed signal and a reference signal;

computing a first difference of the preprocessed signal;

calculating a Hilbert transform of the first difference generating a Hilbert transform signal with potential R-peaks of the QRS-complexes;

calculating a Shannon energy transform of the Hilbert transform signal generating a Shannon energy transform signal to emphasize on the potential R-peaks of the QRS-complexes;

applying histogram analysis on the Shannon transform signal to ablate samples not belonging to QRS-complexes and confirm the potential R-peaks of the QRS-complexes as R-peaks; and mapping the R-peaks onto a time-domain plot of the reference signal to detect their respective Q and R-peaks, resulting in segments each containing a Q-peak, R-peak, and S-peak representing a detected QRS-complex of the ECG signal.

3. The method of claim 2, wherein preprocessing the ECG signal comprises applying two filters generating two signals, one is a preprocessed ECG signal used to detect one or more R-peaks of the QRS-complexes, and the other is a reference ECG signal used to map the detected R-peaks onto and to detect the Q and the S-peaks of the QRS-complexes.

4. The method of claim 2, wherein the histogram analysis applied to the Shannon energy transform signal to ablate time-samples not belonging to QRS-complexes comprising:

computing the histogram of the Shannon energy transform signal to determine an amplitude-band threshold; and eliminating time-samples of the Shannon energy transform signal with an amplitude lower than the amplitude-band threshold.

5. The method of claim 4, wherein non-overlapping windows are applied to the histogram analysis signal keeping only data with the maximum amplitude within the non-overlapping window.

6. The method according to claim 2, wherein detecting the Q and S-peaks after mapping the R-peaks onto the reference signal comprising:

if a polarity of an R-peak in the Shannon energy transform signal was positive, the index of the minimum amplitude within a predetermined time preceding the R-peak corresponded to a Q-peak; and the index of the minimum amplitude within a second predetermined time succeeding the R-peak corresponded to an S-peak; and if the polarity of an R-peak in the Shannon energy transform signal was negative, the index of the maximum amplitude within the predetermined time preceding the R-peak corresponded to a Q-peak; and the index of the maximum amplitude within the second predetermined time succeeding the R-peak corresponded to an S-peak.

7. The method of claim 1, wherein the geometric measure of QRS-angle, QRS$^o$, is calculated using the equation $$QRS^o = \cos^{-1}\left(\frac{\overrightarrow{QR} \cdot \overrightarrow{RS}}{\|\overrightarrow{QR}\| \cdot \|\overrightarrow{RS}\|}\right),$$

where $\overrightarrow{QR}$ is the distance between the Q-peak and the R-peak in the triangle created by connecting the Q, R, and S-peaks, $\overrightarrow{RS}$ is the distance between the R-peak and S-peak.

8. The method of claim 1, wherein the geometric measure of QRS-area is calculated using a trapezoidal rule.

9. The method of claim 1, wherein the geometric measures comprising QRS-height corresponds to an amplitude of an R-peak of the QRS-complex.

10. The method of claim 1, wherein transforming the RGB image to a plurality of gray-scale images through use of a range of different weight values assigned to each plane of the RGB image following the equation $$G_{image}^i = (wt_R * R) + (wt_G * G) + (wt_B * B),$$

where $$G_{image}^i$$

is the i$^{th}$ gray-scale image, i is 1, 2, 3, . . . , and wt$_R$, wt$_G$, and wt$_B$ are the weights of the R, G, and B planes of the RGB image, the sum of the weights (wt$_R$+wt$_G$+wt$_B$) must equal one.

11. The method of claim 1, wherein the saliency threshold (Th$_{int1}$) is iteratively adjusted based on prior experiments to identify different types of QRS-abnormalities.

12. The method according to claim 1, wherein motion artifact and sudden-change-in-baseline are identified using saliency analysis comprising:

computing the absolute maximum amplitude of the first difference of every region between the S-peak of a QRS-complex and the Q-peak of consecutive QRS-complex, SQ regions;

normalizing the absolute maximum amplitudes of the SQ regions, and arranging them in a matrix form constructing a gray-scale image;

computing histogram of the gray-scale image; iteratively comparing every histogram peak to its previous one; and calculating salient intensities corresponding to histogram peaks with a difference value of equal or greater than another predefined threshold, another saliency threshold (Th$_{int2}$); mapping salient intensities indices onto the reference signal; and classifying respective indices on the reference signal as noise.

13. The method according to claim 1, wherein each QRS-complex is normalized through use of fast Fourier transform prior to calculating the geometric measures comprising QRS-angle, QRS-area, and QRS-height.

14. The method according to claim 1, wherein the identified abnormal QRS-complexes are marked on the ECG signal differently depending on the type of abnormality.

15. A computer-implemented method for detecting motion artifact and sudden-change-in-baseline using saliency detection in ECG signals comprising:

receiving an ECG signal with pre-located QRS-complexes, the ECG signal captured by a sensor; and at a residual noise module implemented using at least one processor:

computing the absolute maximum amplitude of the first difference of every region between an S-peak of a QRS-complex and a Q-peak of the consecutive QRS-complex, SQ regions;

normalizing the absolute maximum amplitudes of the SQ regions; generating a gray-scale image by arranging in a matrix form;

computing histogram of the gray-scale image; iteratively comparing every histogram peak to its previous one;

generating a salient gray-scale image by selecting salient pixels from pixels in the gray-scale image based on salient intensities corresponding to histogram peaks with a difference value of more than a predefined threshold;

mapping salient pixel indices of the salient gray-scale image onto the ECG signal;

classifying respective indices on the ECG signal as noise;

filtering the noise from the ECG signal; and outputting the filtered ECG signal.

16. A computer-implemented method for identifying abnormal QRS-complexes in an ECG signal comprising:

receiving an ECG signal with pre-located QRS-complexes, the ECG signal captured by a sensor; and at an identification module implemented using at least one processor:

arranging each type of geometric measures from the QRS-complexes in a three dimensional matrix, the geometric measures belonging to a QRS-complex have the same index across the three dimensional matrix, constructing an RGB image;

generating a plurality of gray-scale images based on the RGB image;

computing histograms of each of the plurality of gray-scale image;

iteratively comparing every histogram peak to its previous one;

generating a plurality of salient gray-scale images by selecting salient pixels from pixels in the plurality of gray-scale images using saliency detection for calculating salient intensities corresponding to histogram peaks with a difference value of more than a predefined threshold;

mapping salient pixel indices of the salient gray-scale images onto the ECG signal;

classifying respective indices on the ECG signal as abnormal QRS complexes; and outputting the abnormal QRS complexes.

17. A computer program product comprising a non-transient storage device comprising instructions that when executed by at least one processor on a computing device, configure the computing device for identifying abnormal QRS-complexes in an ECG signal and configure the computing device to:

receive an ECG signal with detected QRS-complexes, the ECG signal captured by a sensor; and at an identification module implemented using the at least one processor:

calculate a plurality of geometric measures of the QRS-complexes comprising: QRS-angle, QRS-area, and QRS-height;

normalize the geometric measures;

construct an RGB image with three two-dimensional matrices, representing the R, G, and B planes of the RGB image, each matrix corresponds to one of the calculated plurality of geometric measures, the geometric measures belonging to one QRS-complex have the same matrix index across the three two-dimensional matrices;

generate a plurality of gray-scale images based on the RGB image;

compute histograms of each of the plurality of gray-scale image;

iteratively comparing every histogram peak to its previous one;

generate a plurality of salient gray-scale images by selecting salient pixels from pixels in the plurality of gray-scale images based on pixel intensities corresponding to histogram peaks with a difference value of equal or greater than a predefined threshold, a saliency threshold ($Th_{int1}$);

map salient pixels indices of the salient gray-scale images onto the ECG signal;

classify respective indices on the ECG signal as abnormal QRS complexes; and outputting the abnormal QRS complexes.

18. A computing device comprising a processor, a non-transient storage device and a communication device where each of the storage device and the communication device is coupled to the processor, the storage device storing instructions that when executed by the processor, configure the computing device to:

receive an ECG signal with detected QRS-complexes, the ECG signal captured by a sensor; and at an identification module implemented using the processor:

calculate a plurality of geometric measures of the QRS-complexes comprising: QRS-angle, QRS-area, and QRS-height;

normalize the geometric measures;

construct an RGB image with three two-dimensional matrices, representing the R, G, and B planes of the RGB image, each matrix corresponds to one of the calculated plurality of geometric measures, the geometric measures belonging to one QRS-complex have the same matrix index across the three two-dimensional matrices;

generate a plurality of gray-scale images based on the RGB image;

compute histograms of each of the plurality of gray-scale image;

iteratively comparing every histogram peak to its previous one;

generate a plurality of salient gray-scale images by selecting salient pixels from pixels in the plurality of gray-scale image based on pixel intensities corresponding to histogram peaks with a difference value of equal or greater than a predefined threshold, a saliency threshold ($Th_{int1}$);

map salient pixels indices of the salient gray-scale images onto the ECG signal;

classify respective indices on the ECG signal as abnormal QRS complexes; and outputting the abnormal QRS complexes.

* * * * *